(12) United States Patent
Takahata

(10) Patent No.: US 11,590,250 B2
(45) Date of Patent: Feb. 28, 2023

(54) DISPLAY DEVICE AND STERILIZATION DEVICE

(71) Applicant: Japan Display Inc., Tokyo (JP)

(72) Inventor: Masashi Takahata, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 17/476,568

(22) Filed: Sep. 16, 2021

(65) Prior Publication Data

US 2022/0088243 A1    Mar. 24, 2022

(30) Foreign Application Priority Data

Sep. 18, 2020  (JP) .............................. JP2020-157861

(51) Int. Cl.
| A61L 2/10 | (2006.01) |
| G02F 1/1335 | (2006.01) |
| G02F 1/1333 | (2006.01) |
| H05B 47/115 | (2020.01) |

(52) U.S. Cl.
CPC ............ *A61L 2/10* (2013.01); *G02F 1/13338* (2013.01); *G02F 1/133616* (2021.01); *H05B 47/115* (2020.01); *A61L 2202/11* (2013.01); *A61L 2202/14* (2013.01); *G02F 2203/01* (2013.01); *G02F 2203/02* (2013.01)

(58) Field of Classification Search
None
See application file for complete search history.

(56) References Cited

U.S. PATENT DOCUMENTS

| 2011/0115749 | A1* | 5/2011 | Yi ......................... G06F 3/0386 345/175 |
| 2011/0291995 | A1  | 12/2011 | Shr et al. |
| 2014/0293189 | A1* | 10/2014 | Fukunaga ......... G02F 1/133504 349/65 |
| 2017/0153749 | A1* | 6/2017 | Noguchi ............. G06F 3/04164 |
| 2018/0154029 | A1  | 6/2018 | Shr et al. |
| 2019/0030196 | A1* | 1/2019 | Bilenko .................... A61L 2/10 |
| 2021/0290791 | A1* | 9/2021 | Mandaric .................. A61L 2/28 |
| 2021/0338859 | A1* | 11/2021 | Yu ............................. A61L 2/10 |

FOREIGN PATENT DOCUMENTS

JP        2014039876 A     3/2014

\* cited by examiner

*Primary Examiner* — Shan Liu
(74) *Attorney, Agent, or Firm* — K&L Gates LLP

(57) ABSTRACT

According to an aspect, a display device includes: a display panel including a display surface; a sensor configured to detect an external object in proximity to or in contact with the display surface; an ultraviolet light emitter configured to emit ultraviolet light to the display surface; and a controller configured to control an operation of the ultraviolet light emitter. The controller increases an emission amount of ultraviolet light from the ultraviolet light emitter as the object approaches the display surface, and reduces the emission amount of ultraviolet light from the ultraviolet light emitter as the object recedes from the display surface.

16 Claims, 18 Drawing Sheets

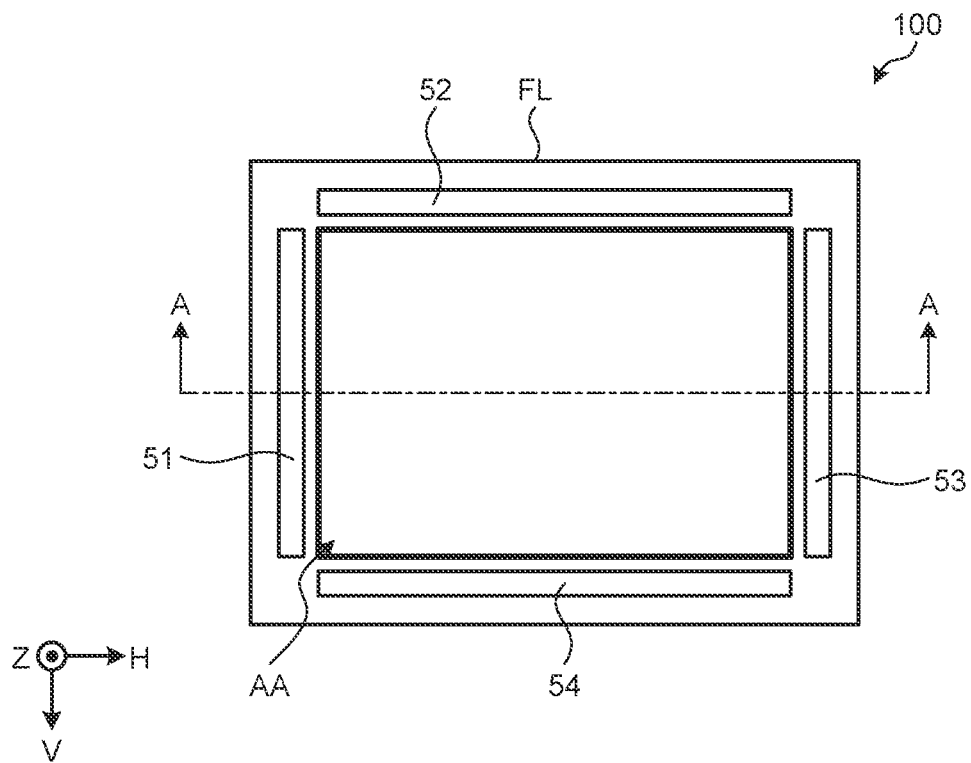
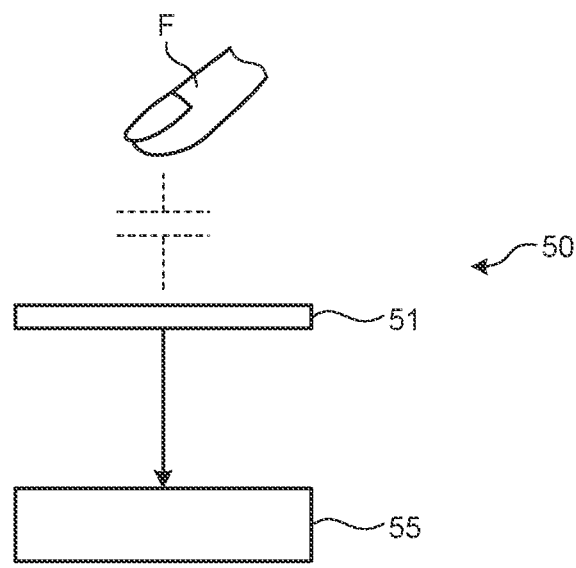

FIG.5

| POSITIONAL RELATION WITH EXTERNAL OBJECT | 4 cm | 3 cm | 2 cm | 1 cm | IN CONTACT |
|---|---|---|---|---|---|
| A: APPROACHING | 0 | 0 | 1 | 3 | 5 |
| B: RECEDING | 1 | 2 | 3 | 4 | 5 |

FIG.18
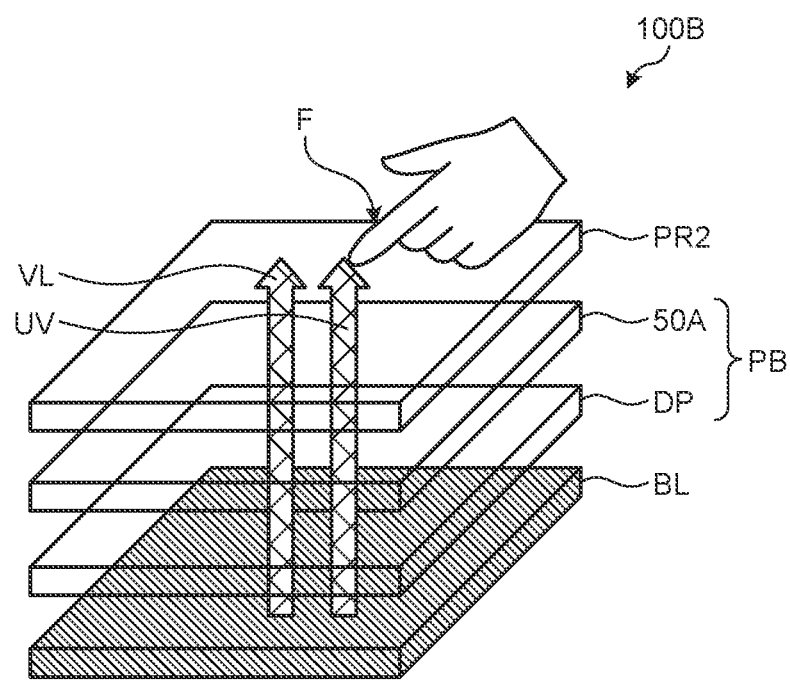
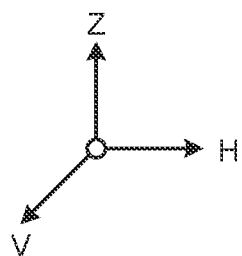

DISPLAY DEVICE AND STERILIZATION DEVICE

CROSS-REFERENCE TO RELATED APPLICATION

This application claims the benefit of priority from Japanese Patent Application No. 2020-157861 filed on Sep. 18, 2020, the entire contents of which are incorporated herein by reference.

BACKGROUND

1. Technical Field

What is disclosed herein relates to a display device and a sterilization device.

2. Description of the Related Art

For a touch panel type display device, a method of sterilizing a contact operation surface using ultraviolet light has been known (for example, Japanese Patent Application Laid-open Publication No. 2014-39876 (JP-A-2014-39876)).

The display device disclosed in JP-A-2014-39876 is capable of switching between emitting and not emitting ultraviolet light, but incapable of increasing or decreasing the emission amount of ultraviolet light in accordance with the need for sterilization.

SUMMARY

According to an aspect, a display device includes: a display panel including a display surface; a sensor configured to detect an external object in proximity to or in contact with the display surface; an ultraviolet light emitter configured to emit ultraviolet light to the display surface; and a controller configured to control an operation of the ultraviolet light emitter. The controller increases an emission amount of ultraviolet light from the ultraviolet light emitter as the object approaches the display surface, and reduces the emission amount of ultraviolet light from the ultraviolet light emitter as the object recedes from the display surface.

According to an aspect, a sterilization device includes: a sensor configured to detect proximity or contact of an external object; an ultraviolet light emitter configured to emit ultraviolet light; and a controller configured to control an operation of the ultraviolet light emitter. The controller increases an emission amount of ultraviolet light from the ultraviolet light emitter as the object approaches the sensor, and reduces the emission amount of ultraviolet light from the ultraviolet light emitter as the object recedes from the sensor.

BRIEF DESCRIPTION OF THE DRAWINGS

FIG. 2 is a plan view illustrating an example of a positional relation between a display panel and a sensor;

FIG. 3 is an explanatory diagram illustrating a configuration in which a proximity operation performed by a user and a contact operation performed by a user are detected by the sensor;

FIG. 5 is a table illustrating an example of controlling the emission amount of ultraviolet light, when the user approaches the display device and when the user recedes from the display device;

FIG. 18 is a conceptual diagram illustrating the order of layering the main components of a display device in a third modification;

DETAILED DESCRIPTION

Figure 1:
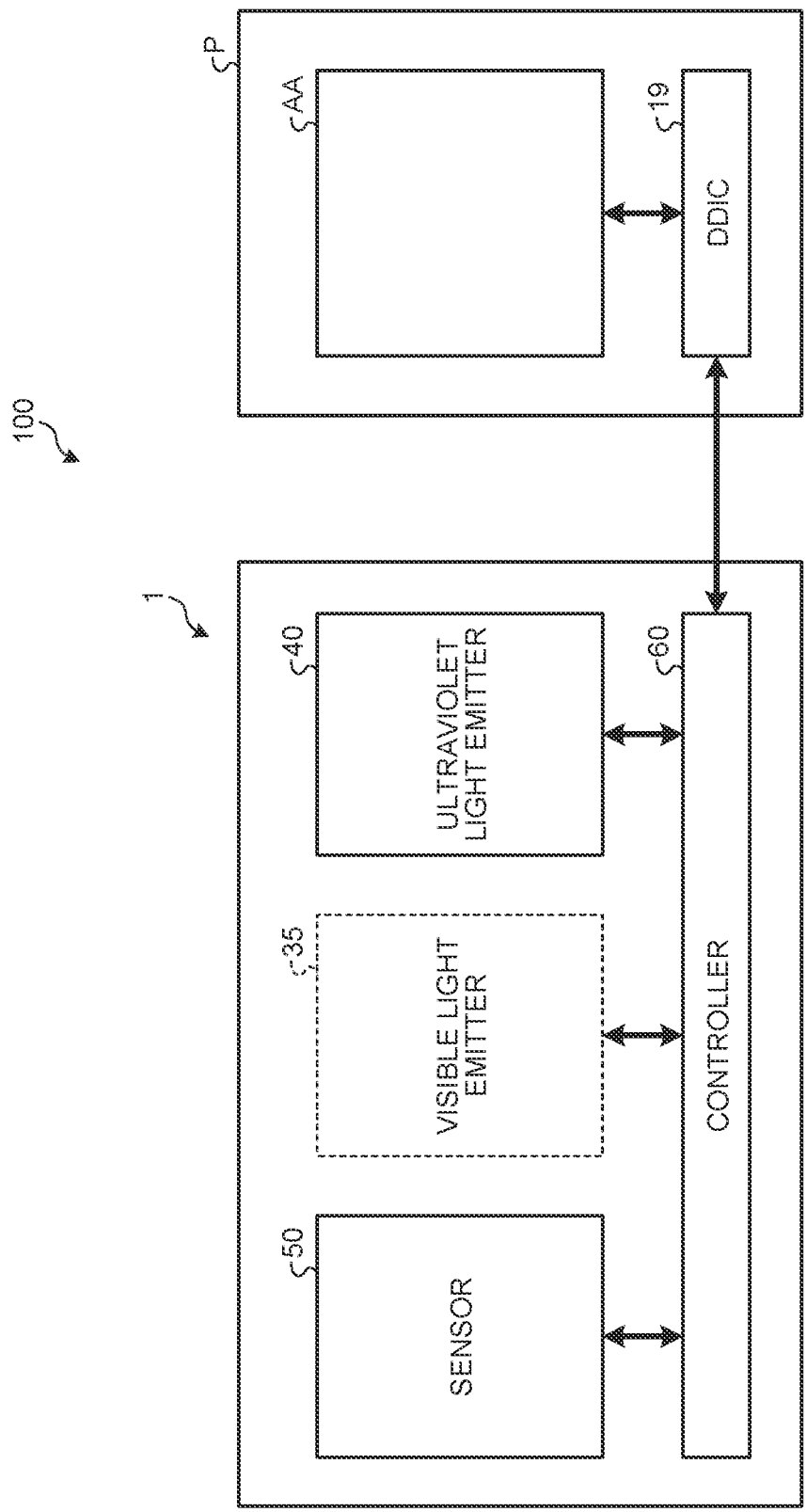
FIG. 1 is a block diagram illustrating an example of a main configuration of a display device provided with a sterilization device.

Hereinafter, embodiments of the present disclosure will be described in detail with reference to the accompanying drawings. What is disclosed herein is merely an example, and the present disclosure naturally encompasses an appropriate modification maintaining the gist of the invention that is easily conceivable by those skilled in the art. To further clarify the description, a width, a thickness, a shape, and the like of each component may be schematically illustrated in the drawings as compared with an actual aspect. However, this is merely an example, and interpretation of the present disclosure is not limited thereto. The same element as that described in the drawing that has already been discussed is denoted by the same reference numeral throughout the present specification and the drawings, and detailed description may be omitted as appropriate.

In this disclosure, when an element is described as being "on" another element, the element can be directly on the other element, or there can be one or more elements between the element and the other element.

First Embodiment

FIG. 1 is a block diagram illustrating an example of a main configuration of a display device 100 provided with a sterilization device 1. The sterilization device 1 includes an ultraviolet light emitter 40, a sensor 50, and a controller 60. The ultraviolet light emitter 40 emits ultraviolet light to an object to be sterilized. Such an object to be sterilized with the light from the ultraviolet light emitter 40 is a display panel P, for example.

The display panel P is provided with a display area AA for displaying an image. A plurality of pixels such as pixels SPix (see FIG. 12), which will be described later, are disposed in the display area AA. The display panel P includes a display driver integrated circuit (DDIC) 19 that controls an operation of the pixels. The DDIC 19 is an integrated circuit in which a plurality of functions including a function of a source driver that supplies a pixel signal to each of the pixels, a function of a gate driver that operates a switching element in the pixel, a function of a timing controller that controls the operation timings of the source driver and the gate driver, and the like are integrated. The display panel P may also include another circuit in which a part of the above-described functions is implemented. In this case, the part of the functions is omitted from the DDIC 19.

The ultraviolet light emitter 40 includes at least a sterilization lamp that emits light UV including ultraviolet light in accordance with the power supply. Hereinafter, unless otherwise specified, when a sterilization lamp is simply referred to without a reference numeral, it denotes a sterilization lamp provided in the ultraviolet light emitter 40. The ultraviolet light emitter 40 may also be an ultraviolet light emitting unit in which a sterilization lamp and a circuit for controlling the current and voltage supplied to the sterilization lamp are combined. The sterilization lamp may be a light emitting diode (LED) that emits ultraviolet light, or may be a sterilization lamp of a fluorescent lamp type including quartz glass serving as a tube body that is not coated with what is called a fluorescent substance. In this example, the quartz glass is an example of a light-transmitting medium through which ultraviolet light is favorably transmitted. However, it is not limited thereto, and any other member having a similar function may also be used.

More specifically, when the ultraviolet light emitted from the sterilization lamp is ultraviolet light with a peak wavelength around 222 nm, sterilizing effects of ultraviolet light and prevention of harmful effects on human beings can be well balanced. When the ultraviolet light emitted from the sterilization lamp is ultraviolet light with a peak wavelength of around 253.7 nm, the sterilizing effects of ultraviolet light can be improved even more. However, the peak wavelength of ultraviolet light is not limited thereto. For example, the peak wavelength of ultraviolet light is preferably between 200 nm and 280 nm, or between 200 nm and 240 nm. It is also preferable to provide the sterilization lamp that can emit ultraviolet light with wavelength of about ±20 nm, or more preferably, about ±10 nm around the peak wavelength of the ultraviolet light, and such that the ultraviolet light is emitted at an intensity that is effective for sterilization.

The sensor 50 detects a proximity operation performed by a user and a contact operation performed by a user. The user is a user who uses an object to be sterilized with the light emitted from the ultraviolet light emitter 40 (for example, the display panel P).

FIG. 2 is a plan view illustrating an example of a positional relation between the display panel P and the sensor 50. In the present specification, a plan view is a view when a plane extending in an H direction and a V direction (H-V plane) is viewed as a front surface. As illustrated in FIG. 2, the sensor 50 is disposed around the display area AA. More specifically, the sensor 50 includes detection electrodes 51, 52, 53, and 54 disposed along the respective four sides of the rectangular display area AA and also includes a detection circuit 55 (see FIG. 3), which will be described later. The display area AA illustrated in FIG. 2 is formed in a rectangular shape. However, the specific shape of the display area AA is not limited thereto and may also be formed in a polygonal shape having five sides or more or three sides, or some or all of the sides may be formed in an arc shape. The sensor 50 includes a plurality of detectors disposed along the outer peripheral edge of the display area AA.

The detection electrodes 51 and 53 illustrated in FIG. 2 are disposed along two sides in the V direction of the four sides of the display area AA so as to face each other in the H direction with the rectangular display area AA interposed therebetween. The lengths of the detection electrodes 51 and 53 in the V direction are substantially the same as the lengths of the two sides of the display area AA in the V direction. The detection electrodes 52 and 54 illustrated in FIG. 2 are disposed along two sides in the H direction of the four sides of the display area AA so as to face each other in the V direction with the rectangular display area AA interposed therebetween. The lengths of the detection electrodes 52 and 54 in the H direction are substantially the same as the lengths of the two sides of the display area AA in the H direction. The positional relation between the display panel P and the detection electrodes 51, 52, 53, and 54 is supported by a housing FL of the display device 100. The housing FL contains therein the sterilization device 1 and the display panel P illustrated in FIG. 1.

Of the four sides of the display area AA illustrated in FIG. 2, a direction along one of the two sides orthogonal to each other is referred to as the H direction. A direction along the other one of the two sides is referred to as the V direction. A direction orthogonal to the H direction and the V direction is referred to as a Z direction.

FIG. 3 is an explanatory diagram illustrating a configuration in which a proximity operation performed by a user and a contact operation performed by a user are detected by the sensor 50. The detection electrode 51 is coupled to the detection circuit 55. The detection circuit 55 detects current produced by the self-capacitance of the detection electrode 51. As illustrated in FIG. 3, when an external object such as a finger F of the user is in proximity to or in contact with the detection electrode 51, mutual-capacitance is generated between the detection electrode 51 and the finger F, thereby changing the self-capacitance of the detection electrode 51. Consequently, the amount of current detected by the detection circuit 55 is changed in accordance with the presence and absence of an external object, which is in proximity to or in contact with the detection electrode 51, and the distance between the detection electrode 51 and the object. The sensor 50 detects a proximity operation performed by the user or a contact operation performed by the user, on the basis of the current detected by the detection circuit 55.

The sensor 50 detects an external object multiple times with a lapse of time. More specifically, for example, the sensor 50 repeatedly detects an external object at a predetermined cycle. On the basis of the time series variation pattern of the current detected by the detection circuit 55, it is possible to determine whether the position of the external object is changing such that the external object is approaching the sensor 50, and whether the position of the external object is changing such that the external object is receding from the sensor 50.

The degree of change in self-capacitance of each of the detection electrodes 51, 52, 53, and 54 is changed in accordance with a position in the H-V plane view of a proximity operation or a contact operation performed by the user within the display area AA as illustrated in FIG. 2. Thus, by determining the degree of change in self-capacitance of each of the detection electrodes 51, 52, 53, and 54 on the basis of the current detected by the detection circuit 55, it is also possible to determine the position in the H-V plane view of the proximity operation performed by the user or the contact operation performed by the user.

In the description referring to FIG. 3, the detection mechanism is described using the detection electrode 51 as an example. However, as is the case with the detection electrode 51, the detection electrodes 52, 53, and 54 are also coupled to the detection circuit 55. The detection electrodes 51, 52, 53, and 54 may be coupled to the respective detection circuits 55 provided individually or may share the detection circuit 55. The sensor 50 of the embodiment detects the proximity operation to the display panel P performed by the user and the contact operation on the display panel P performed by the user, on the basis of the current from each of the detection electrodes 51, 52, 53, and 54 detected by the detection circuit 55.

Figure 4:
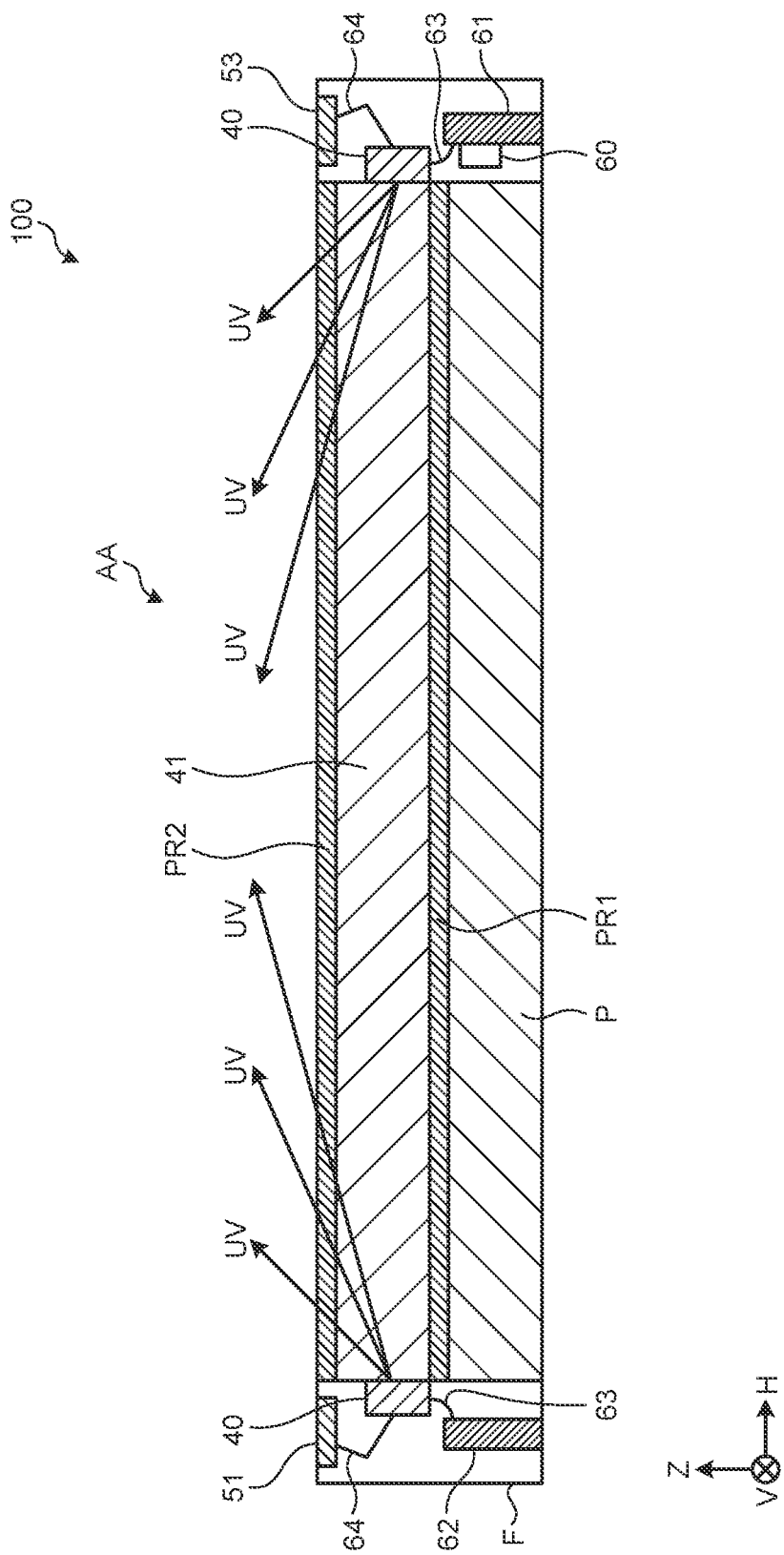
FIG. 4 is a sectional view cut along line A-A in FIG. 2.

FIG. 4 is a sectional view cut along line A-A in FIG. 2. The display panel P is provided with a protection layer PR1 on the display surface side of the display area AA. A light guide plate 41 is provided on the side opposite to the display panel P with the protection layer PR1 interposed therebetween. A protection layer PR2 is provided on the side opposite to the protection layer PR1 with the light guide plate 41 interposed therebetween. The display surface side of the protection layer PR2 is exposed to the outside. That is, in the display device 100, the display panel P, the protection layer PR1, the light guide plate 41, and the protection layer PR2 are layered in the order as listed, from the display panel P side toward the protection layer PR2 side in the Z direction.

As illustrated in FIG. 4, the detection electrodes 51 and 53 are placed closer to the display surface side than the ultraviolet light emitter 40 is. In FIG. 4, the positions of the detection electrodes 51 and 53 in the Z direction are the same as that of the protection layer PR2. However, the surface of the detection electrodes 51 and 53 on the display surface side may also be covered by the protection layer PR2 or another protection layer. Although not illustrated in FIG. 4, the positions of the detection electrodes 52 and 54 in the Z direction are the same as those of the detection electrodes 51 and 53 in the Z direction. In FIG. 4, the thickness of the detection electrodes 51 and 53 in the Z direction is the same as that of the protection layer PR2 in the Z direction. However, FIG. 4 is a schematic illustration and does not exactly represent the relation between the thickness of the detection electrodes 51, 52, 53, and 54 in the Z direction, and the thickness of the protection layer PR2 in the Z direction.

The ultraviolet light emitter 40 is disposed so that the position of the ultraviolet light emitter 40 in the Z direction is the same as that of the light guide plate 41. More specifically, for example, as illustrated in FIG. 4, a plurality of the ultraviolet light emitters 40 are disposed so as to face each other in the H direction with the light guide plate 41 interposed therebetween. Although not illustrated, the ultraviolet light emitters 40 may also be disposed so as to face each other in the V direction with the light guide plate 41 interposed therebetween. The ultraviolet light emitters 40 emit the light UV to the display surface side. The light UV transmits through the light guide plate 41 and the protection layer PR2, and sterilizes the exposed surface of the protection layer PR2 on the display surface side. The sterilization lamp is provided so as to emit the light UV to the display surface side. More concretely, by providing a reflective surface part, which is capable of favorably reflecting the ultraviolet light, on the display panel P side of the sterilization lamp and on a side of the sterilization lamp opposite to the light guide plate 41 side, it is possible to guide the light UV toward the protection layer PR2 side more favorably. For example, the reflective surface part is coated with a material such as aluminum capable of reflecting ultraviolet light in a favorable manner.

The ultraviolet light emitter 40 and the sensor 50 are coupled to the controller 60. FIG. 4 illustrates an example of a configuration in which the controller 60 is provided on a substrate 61. In the example illustrated in FIG. 4, a substrate 62 is disposed on a side opposite to the substrate 61 with the display panel P interposed therebetween. The positions of the substrate 61 and the substrate 62 in the Z direction are closer to the display panel P side than the detection electrodes 51 and 53 are. Although not illustrated, the substrate 61 and the substrate 62 are electrically coupled to each other. Wiring that couples the controller 60 and other components is formed on the substrate 61 and the substrate 62. The ultraviolet light emitter 40 illustrated in FIG. 4 is coupled to the controller 60 by being coupled to the substrate 61 or the substrate 62 via wiring 63. The detection electrode 51 illustrated in FIG. 4 is coupled to the controller 60 by being coupled to the substrate 62 via wiring 64. The detection electrode 53 illustrated in FIG. 4 is coupled to the controller 60 by being coupled to the substrate 61 via the wiring 64. Although not illustrated, the detection electrodes 52 and 54 are also coupled to the controller 60 via wiring similar to the wiring 64 or the like. For example, a substrate similar to the substrate 62 may also be disposed on the display panel P side of the detection electrodes 52 and 54. Although not illustrated in FIG. 4, for example, the detection circuit 55 is mounted on the substrates 61 and 62.

The controller 60 is a circuit that controls the emission amount of ultraviolet light from the ultraviolet light emitter 40 on the basis of the distance between the sensor 50 and the user in accordance with a proximity operation performed by the user or a contact operation performed by the user detected by the sensor 50. The controller 60 increases the emission amount of ultraviolet light from the ultraviolet light emitter 40 as the distance between the user and the sensor 50 decreases. Any specific method for controlling the emission amount of ultraviolet light from the ultraviolet light emitter 40 can be employed. For example, the emission amount of ultraviolet light from the ultraviolet light emitter 40 may be controlled by controlling the length of light emission time of the sterilization lamp per unit time, by controlling the light emission intensity of the sterilization lamp provided such that the light emission intensity is controllable, or by a combination of the two methods.

In the embodiment, the detection electrodes 51, 52, 53, and 54 are provided so as to be able to individually detect an external object such as a finger F. Thus, some of the detection electrodes 51, 52, 53, and 54 may detect the external object at the same time. In this case, the shortest distance from the external object among the detected distances therefrom is handled as the distance between the sensor 50 and the user.

In the embodiment, the controller 60 controls the emission amount of ultraviolet light from the ultraviolet light emitter 40 such that the amount of decrease in the emission amount of ultraviolet light with respect to the amount of change in distance between the external object and the display surface when the external object recedes from the display surface is smaller than the amount of increase in the emission amount of ultraviolet light with respect to the amount of change in distance between the external object and the display surface when the external object approaches the display surface. In other words, the controller 60 controls the emission amount of ultraviolet light from the ultraviolet light emitter 40 such that a rate of decrease in the emission amount of ultraviolet light with respect to the distance between the external object and the display surface when the external object recedes from the display surface is smaller than a rate of increase in the emission amount of ultraviolet light with respect to the distance between the external object and the display surface when the external object approaches the display surface.

FIG. 5 is a table illustrating an example of controlling the emission amount of ultraviolet light, when the user approaches the display device 100 and when the user recedes from the display device 100. With reference to FIG. 5, an example of controlling the operation of the ultraviolet light emitter 40 by the controller 60 will be described. In FIG. 5, for easy understanding, the emission amount of ultraviolet light is quantified into numerical values of six levels: 0, 1, 2, 3, 4, and 5. The emission amount of ultraviolet light is increased with an increase in the numerical value. When the emission amount of ultraviolet light is 5, the "sterilization lamp is controlled to be ON at the maximum light intensity". When the emission amount of ultraviolet light is 1, the "sterilization lamp is controlled to be ON at the minimum light intensity". When the emission amount of ultraviolet light is 0, the "sterilization lamp is controlled to be OFF".

FIG. 5 conceptually illustrates the change in the positional relation between the user and the display device 100 in a case where the external object is "A: approaching" and in a case where the external object is "B: receding". The case where an external object is "A: approaching" is a case where the position of an external object such as a finger F is changed by the user such that the external object approaches the display device 100 from a position away from the display device 100. The case where an external object is "B: receding" is a case where the position of an external object such as a finger F is changed by the user such that the external object recedes from the display device 100 from a position in proximity to or in contact with the display device 100.

When the external object is "A: approaching", as long as the distance between the display device 100 and the external object exceeds 2 cm, the controller 60 sets the emission amount of ultraviolet light from the ultraviolet light emitter 40 to 0. When the external object is "A: approaching", and when the sensor 50 detects that the distance between the display device 100 and the external object reaches 2 cm, the controller 60 sets the emission amount of ultraviolet light from the ultraviolet light emitter 40 to 1. When the external object is "A: approaching", and when the sensor 50 detects that the distance between the display device 100 and the external object reaches 1 cm, the controller 60 sets the emission amount of ultraviolet light from the ultraviolet light emitter 40 to 3. When the external object is "A: approaching", and when the sensor 50 detects that the distance between the display device 100 and the external object is in a contact state (0 cm), the controller 60 sets the emission amount of ultraviolet light from the ultraviolet light emitter 40 to 5.

When the external object is "B: receding", as long as the sensor 50 detects that the distance between the display device 100 and the external object is in a contact state (0 cm), the controller 60 sets the emission amount of ultraviolet light from the ultraviolet light emitter 40 to 5. When the external object is "B: receding", and when the sensor 50 detects that the distance between the display device 100 and the external object reaches 1 cm, the controller 60 sets the emission amount of ultraviolet light from the ultraviolet light emitter 40 to 4. When the external object is "B: receding", and when the sensor 50 detects that the distance between the display device 100 and the external object reaches 2 cm, the controller 60 sets the emission amount of ultraviolet light from the ultraviolet light emitter 40 to 3. When the external object is "B: receding", and when the sensor 50 detects that the distance between the display device 100 and the external object reaches 3 cm, the controller 60 sets the emission amount of ultraviolet light from the ultraviolet light emitter 40 to 2. When the external object is "B: receding", and when the sensor 50 detects that the distance between the display device 100 and the external object reaches 4 cm, the controller 60 sets the emission amount of ultraviolet light from the ultraviolet light emitter 40 to 1. Although not illustrated in FIG. 5, when the external object is "B: receding", and when the sensor 50 detects that the distance between the display device 100 and the external object exceeds 4 cm, the controller 60 may set the emission amount of ultraviolet light from the ultraviolet light emitter 40 to 0.

In the embodiment, the emission amount of the ultraviolet light from the ultraviolet light emitter 40 is set to the maximum (5), when the detection circuit 55 detects the current, which is detected when the user is performing a contact operation of an external object such as the finger F on the surface on the display surface side of the protection layer PR2 of the display device 100. "In contact" in FIG. 5 indicates this state.

On the other hand, a reference of the distance between the user and the display device 100 to be used for setting the emission amount of ultraviolet light from the ultraviolet light emitter 40 to the minimum (1) that is not zero (0), is not limited to "2 cm" when the external object is "A: approaching" or "4 cm" when the external object is "B: receding" illustrated in FIG. 5. The reference can be set to an arbitrary value. For example, in a case where the external object is "B: receding", the emission amount of ultraviolet light from the ultraviolet light emitter 40 may be set to zero (0) (an Off state) when the sensor 50 detects no external object, and the emission amount of ultraviolet light from the ultraviolet light emitter 40 may not be set to zero (0) (an On state) when the sensor 50 detects an external object. Even when the sensor 50 detects an external object, the ultraviolet light emitter 40 may not be turned ON until a current corresponding to a predetermined threshold of the distance between the display device 100 and the user is detected by the detection circuit 55. In this manner, the control pattern of the emission amount of ultraviolet light from the ultraviolet light emitter 40 is not limited to the example illustrated in FIG. 5.

The controller 60 can distinguish between whether the position change of the external object with respect to the sensor 50 corresponds to "A: approaching" or "B: receding". More specifically, for example, the controller 60 includes a memory that holds at least the latest one or more pieces, among pieces of data (for example, current values) indicating the results of operations of detecting the external object performed multiple times by the sensor 50 with a lapse of time. The controller 60 distinguishes between whether the external object is "A: approaching" or "B: receding", based on the relation of the distance between the display device 100 and an external object indicated in the data stored in the memory, and the distance between the display device 100 and the external object indicated in the latest detection result obtained by the sensor 50.

Figure 6:
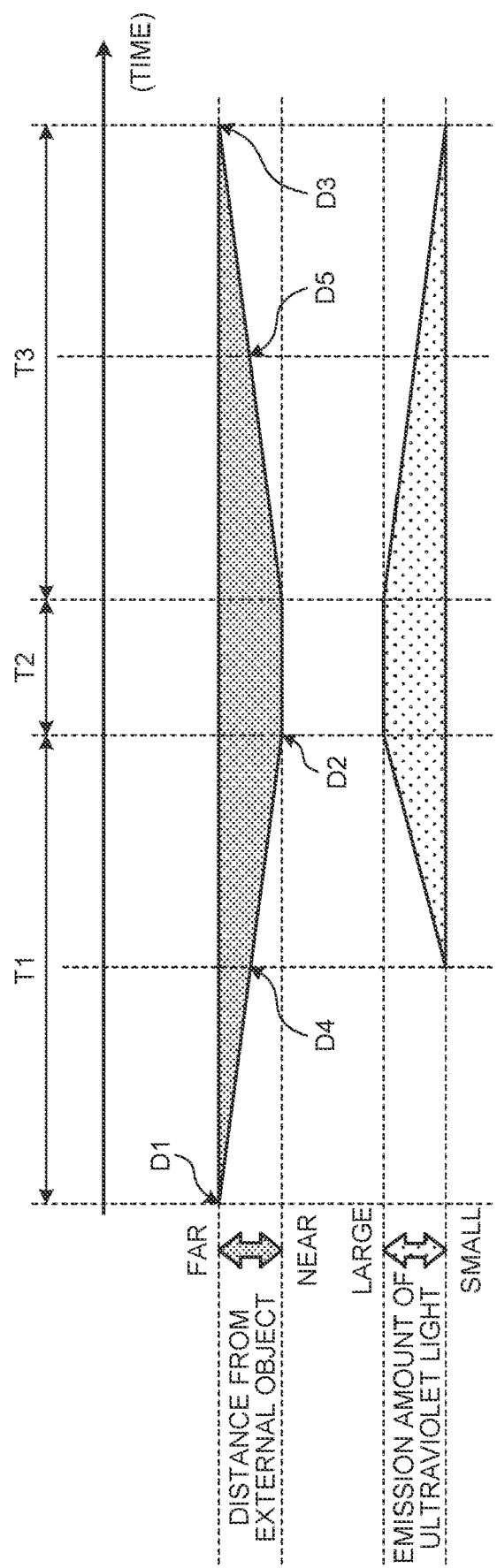
FIG. 6 is a time chart illustrating an example of a relation between the distance from an external object detected by the sensor and the emission amount of ultraviolet light.

FIG. 6 is a time chart illustrating an example of a relation between the distance from an external object detected by the sensor 50 and the emission amount of ultraviolet light from the ultraviolet light emitter 40. In FIG. 6, the external object is "A: approaching" during period T1, whereby the distance between the display device 100 and the external object decreases from distance D1 to distance D2. For example, distance D1 is a distance of "4 cm" illustrated in FIG. 5. For example, distance D2 is a distance of "in contact" illustrated in FIG. 5. In FIG. 6, the distance between the display device 100 and the external object is not changed during period T2 and is kept at distance D2. In FIG. 6, the external object is "B: receding" during period T3, whereby the distance between the display device 100 and the external object increases from distance D2 to distance D3. For example, distance D3 is a distance of "4 cm" illustrated in FIG. 5.

As illustrated in FIG. 6, when the external object is "A: approaching" during period T1, the controller 60 does not turn ON the ultraviolet light emitter 40 until the distance between the display device 100 and the external object reaches distance D4. For example, distance D4 is a distance of "2 cm" illustrated in FIG. 5. When the external object is "A: approaching" during period T1, the controller 60 controls the lighting of the ultraviolet light emitter 40 such that the emission amount of ultraviolet light from the ultraviolet light emitter 40 is increased as the distance between the display device 100 and the external object decreases from distance D4 to distance D2. While the distance between the display device 100 and the external object is kept at distance D2 during period T2, the controller 60 controls the lighting of the ultraviolet light emitter 40 such that the emission amount of ultraviolet light from the ultraviolet light emitter 40 is maintained. When the external object is "B: receding" during period T3, the controller 60 controls the lighting of the ultraviolet light emitter 40 such that the emission amount of ultraviolet light from the ultraviolet light emitter 40 is reduced as the distance between the display device 100 and the external object increases from distance D2 via distance D5 to distance D3. Distance D5 is the same distance as distance D4.

As illustrated in FIG. 6, the emission amount of ultraviolet light corresponding to distance D5 when the external object is "B: receding", is greater than the emission amount of ultraviolet light corresponding to distance D4 when the external object is "A: approaching". This is because the controller 60 controls the emission amount of ultraviolet light from the ultraviolet light emitter 40 such that the amount of decrease in the emission amount of ultraviolet light with respect to the amount of change in distance between the external object and the display surface when the external object recedes from the display surface is smaller than the amount of increase in the emission amount of ultraviolet light with respect to the amount of change in distance between the external object and the display surface when the external object approaches the display surface. In other words, this is because the controller 60 controls the emission amount of ultraviolet light from the ultraviolet light emitter 40 such that the rate of decrease in the emission amount of ultraviolet light with respect to the distance between the external object and the display surface when the external object recedes from the display surface is smaller than the rate of increase in the emission amount of ultraviolet light with respect to the distance between the external object and the display surface when the external object approaches the display surface.

Figure 7:
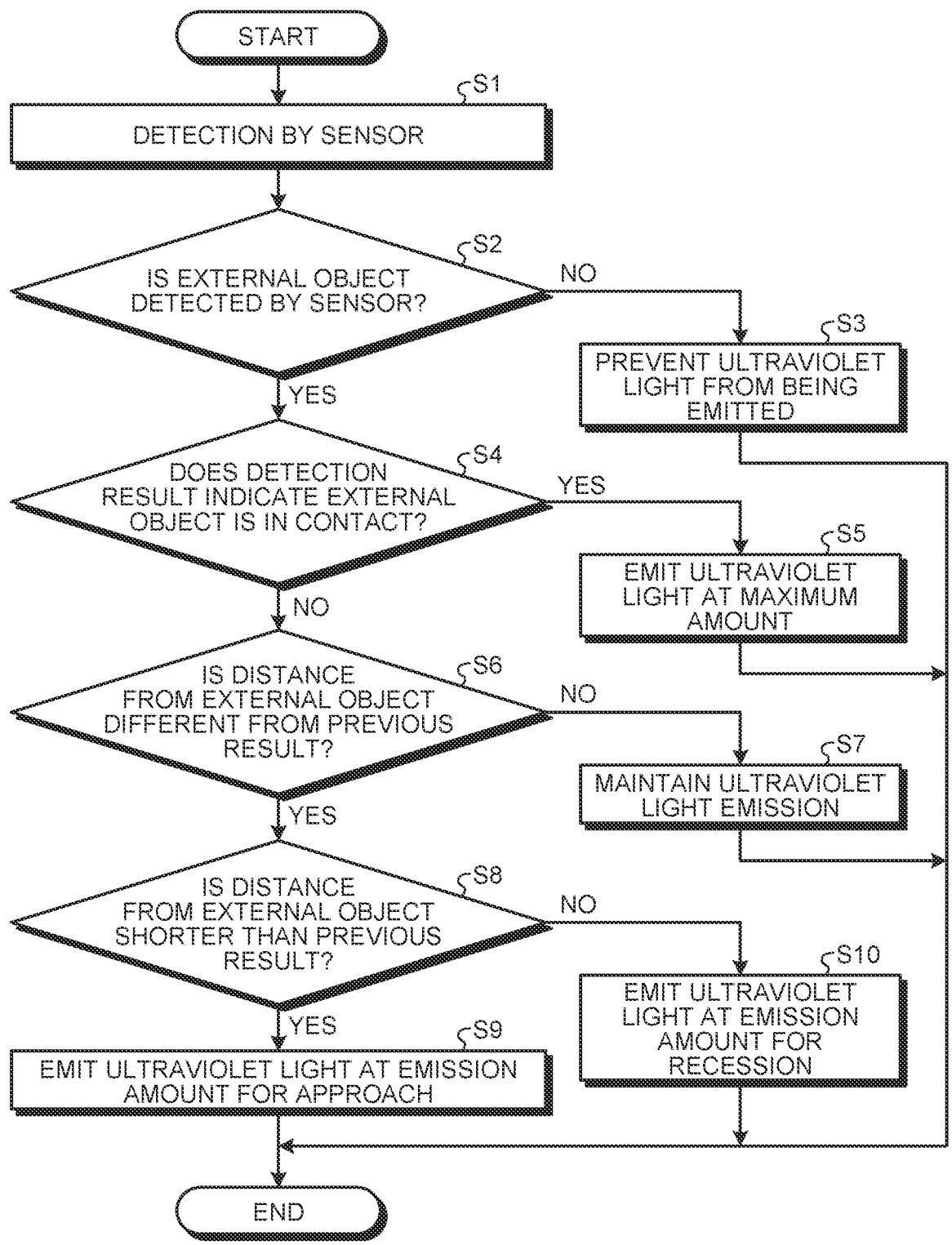
FIG. 7 is a flowchart illustrating a process performed by a controller.

FIG. 7 is a flowchart illustrating a process performed by the controller 60. First, the sensor 50 performs detection of an external object (step S1). The controller 60 determines whether an external object is detected in the process at step S1 (step S2). When an external object is not detected in the process at step S1 (No at step S2), the controller 60 does not turn ON the ultraviolet light emitter 40, and prevents ultraviolet light from being emitted (step S3).

When the external object is detected in the process at step S1 (Yes at step S2), the controller 60 determines whether the detection result obtained in the process at step S1 indicates that the external object is in contact with the display device 100 (step S4). When the detection result obtained in the process at step S1 indicates that the external object is in contact with the display device 100 (Yes at step S4), the controller 60 controls the lighting of the ultraviolet light emitter 40 such that the emission amount of ultraviolet light from the ultraviolet light emitter 40 becomes maximum (step S5).

When the detection result obtained in the process at step S1 does not indicate that the external object is in contact with the display device 100 (No at step S4), the controller 60 determines whether the distance between the display device 100 and the external object in the latest detection result obtained in the process at step S1 is different from that in a detection result obtained immediately therebefore, that is, the previous detection result (step S6). The process at step S6 is a determination process to check whether the distance between the display device 100 and the external object is changed. In the process at step S6, the controller 60 may determine whether the latest detection result obtained in the process at step S1 indicates the same distance as that in the previous detection result.

When the distance between the display device 100 and the external object in the latest detection result obtained in the process at step S1 is the same as that in the previous detection result (No at step S6), the controller 60 controls the lighting of the ultraviolet light emitter 40 such that the emission amount of ultraviolet light from the ultraviolet light emitter 40 is maintained (step S7).

When the distance between the display device 100 and the external object in the latest detection result obtained in the process at step S1 is different from that in the previous detection result (Yes at step S6), the controller 60 determines whether the distance in the latest detection result obtained in the process at step S1 is shorter than that in the previous detection result (step S8). The process at step S8 is a determination process to check whether the distance between the display device 100 and the external object is reduced or increased. In the process at step S8, the controller 60 may determine whether the distance in the latest detection result obtained in the process at step S1 is longer than that in the previous detection result.

When the distance in the latest detection result obtained in the process at step S1 is shorter than that in the previous detection result (Yes at step S8), the controller 60 controls the lighting of the ultraviolet light emitter 40 such that the ultraviolet light is emitted at an emission amount for the approach of the external object (step S9). The emission of ultraviolet light at an emission amount for the approach of the external object is, for example, the emission of ultraviolet light at an emission amount when the external object is "A: approaching" described above. When the distance in the latest detection result obtained in the process at step S1 is longer than that in the previous detection result (No at step S8), the controller 60 controls the lighting of the ultraviolet light emitter 40 such that the ultraviolet light is emitted at an emission amount for the recession of the external object (step S10). The emission of ultraviolet light at an emission amount for the recession of the external object is, for example, the emission of ultraviolet radiation at an emission amount when the external object is "B: receding" described above.

The above describes an example in which the amount of decrease in the emission amount of ultraviolet light with respect to the amount of change in distance between the external object and the display surface when the external object recedes from the display surface is smaller than the amount of increase in the emission amount of ultraviolet light with respect to the amount of change in distance between the external object and the display surface when the external object approaches the display surface. However, the lighting control of the ultraviolet light emitter 40 by the controller 60 is not limited thereto. For example, the rate of increase in the emission amount of ultraviolet light when the external object approaches the sensor 50 may be the same as the rate of decrease in the emission amount of ultraviolet light when the external object recedes from the sensor 50.

As described above, according to the first embodiment, the display panel P including the display surface, the sensor 50 that detects the external object in proximity to or in contact with the display surface, the ultraviolet light emitter 40 that emits ultraviolet light to the display surface, and the controller 60 that controls the operation of the ultraviolet light emitter 40 are provided. The controller 60 increases the emission amount of ultraviolet light from the ultraviolet light emitter 40 as the external object approaches the display surface, and reduces the emission amount of ultraviolet light from the ultraviolet light emitter 40 as the external object recedes from the display surface.

In this manner, it is possible to increase the emission amount of ultraviolet light as the external object approaches. It is also possible to reduce the emission amount of ultraviolet light as the external object recedes. Thus, it is possible to increase and reduce the emission amount of ultraviolet light. When the external object approaches the display surface, infection by pathogens such as bacteria may be caused by contact of the external object therewith. Thus, in a case where the need for sterilization increases, it is possible, by increasing the emission amount of ultraviolet light, to perform more effective sterilization with the need for sterilization.

The amount of decrease in the emission amount of ultraviolet light with respect to the amount of change in distance between the external object and the display surface when the external object recedes from the display surface is smaller than the amount of increase in the emission amount of ultraviolet light with respect to the amount of change in distance between the external object and the display surface when the external object approaches the display surface. In this manner, it is possible to carry out sterilization for a longer period of time, after the external object has moved away. Thus, pathogens that may be transmitted from the external object can be sterilized with reliability after the external object has receded.

The sensor 50 includes the electrodes (for example, the detection electrodes 51, 52, 53, and 54) and detects the external object on the basis of the change in capacitance of the electrodes. In this manner, it is possible to detect the external object with a simple configuration.

The electrodes are disposed along the outer periphery of the display area formed in a polygonal shape that displays an image on the display surface. In this manner, it is possible to detect the external object in the proximity of the display panel P.

In the first embodiment described with reference to FIG. 1 to FIG. 7, the entire display surface of the display area AA is sterilized by turning ON the ultraviolet light emitter 40. Alternatively, as a modification of the embodiment described with reference to FIG. 8 to FIG. 10, which will be described below, a part of the display area AA including the position where the finger F is in proximity to or in contact with the display area AA may be sterilized.

First Modification

Figure 8:
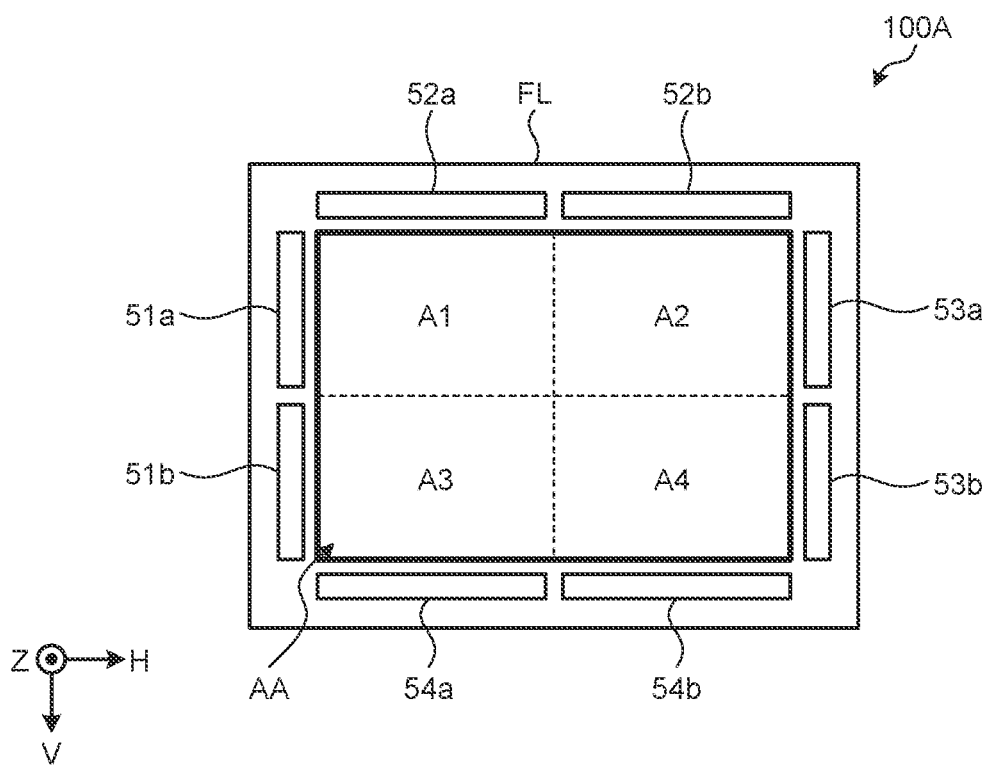
FIG. 8 is a plan view illustrating an example of a configuration of a display device including a plurality of partial detection areas A1, A2, A3, and A4.

FIG. 8 is a plan view illustrating an example of a configuration of a display device 100A including a plurality of partial detection areas A1, A2, A3, and A4. As illustrated in FIG. 8, a detection electrode 51a and a detection electrode 51b, which are provided along one side in the V direction of the four sides of the rectangular display area AA in the H-V view, are arranged in the V direction. The lengths of the detection electrode 51a and the detection electrode 51b in the V direction are the same. The detection electrode 51a and the detection electrode 51b are electrodes obtained by dividing the detection electrode 51 described with reference to FIG. 2 into two in the V direction and are not in contact with each other.

A detection electrode 53a and a detection electrode 53b, which are provided along the other side in the V direction of the four sides of the display area AA, are arranged in the V direction. The lengths of the detection electrode 53a and the detection electrode 53b in the V direction are the same. The detection electrode 53a and the detection electrode 53b are electrodes obtained by dividing the detection electrode 53 described with reference to FIG. 2 into two in the V direction and are not in contact with each other.

A detection electrode 52a and a detection electrode 52b, which are provided along one side in the H direction of the four sides of the display area AA, are arranged in the H direction. The lengths of the detection electrode 52a and the detection electrode 52b in the H direction are the same. The detection electrode 52a and the detection electrode 52b are electrodes obtained by dividing the detection electrode 52 described with reference to FIG. 2 into two in the H direction and are not in contact with each other.

A detection electrode 54a and a detection electrode 54b, which are provided along the other side in the H direction of the four sides of the display area AA, are arranged in the H direction. The lengths of the detection electrode 54a and the detection electrode 54b in the H direction are the same. The detection electrode 54a and the detection electrode 54b are electrodes obtained by dividing the detection electrode 54 described with reference to FIG. 2 into two in the H direction and are not in contact with each other.

The detection electrodes 51a, 51b, 52a, 52b, 53a, 53b, 54a, and 54b are individually coupled to the detection circuit 55 described above. In the display device 100A, an external object is individually detected using each of the detection electrodes 51a, 51b, 52a, 52b, 53a, 53b, 54a, and 54b. In this manner, the display device 100A can determine which of the partial detection areas A1, A2, A3, and A4 the external object, which is in contact with or in proximity to the display area AA, is in contact with or closest to.

Each of the partial detection areas A1, A2, A3, and A4 is a rectangular area. The detection electrode 51a is placed along one of the four sides of the partial detection area A1, and the detection electrode 52a is placed along another side, which is orthogonal to the one side. The detection electrode 52b is placed along one of the four sides of the partial detection area A2, and the detection electrode 53a is placed along another side, which is orthogonal to the one side. The detection electrode 51b is placed along one of the four sides of the partial detection area A3, and the detection electrode 54a is placed along another side, which is orthogonal to the one side. The detection electrode 54b is placed along one of the four sides of the partial detection area A4, and the detection electrode 53b is placed along another side, which is orthogonal to the one side.

For example, assume that an external object is in contact with or closest to the partial detection area A1. In this case, the position of the external object indicated by the detection results obtained by using the detection electrode 51a and the detection electrode 52a is located closer than the positions thereof indicated by the detection results obtained by using the detection electrodes 51b, 52b, 53a, 53b, 54a, and 54b are.

Assume that an external object is in contact with or closest to the partial detection area A2. In this case, the position of the external object indicated by the detection results obtained by using the detection electrode 52b and the detection electrode 53a is located closer than the positions thereof indicated by the detection results obtained by using the detection electrodes 51a, 51b, 52a, 53b, 54a, and 54b are.

Assume that an external object is in contact with or closest to the partial detection area A3. In this case, the position of the external object indicated by the detection results obtained by using the detection electrode 51b and the detection electrode 54a is located closer than the positions thereof indicated by the detection results obtained by using the detection electrodes 51a, 52a, 52b, 53a, 53b, and 54b are.

Assume that an external object is in contact with or closest to the partial detection area A4. In this case, the position of the external object indicated by the detection results obtained by using the detection electrode 53b and the detection electrode 54b is located closer than the positions thereof indicated by the detection results obtained by using the detection electrodes 51a, 51b, 52a, 52b, 53a, and 54a are.

In this manner, with combinations of the detection results of the external object obtained by using the electrodes arranged in the H direction, and the detection results of the external object obtained by using the electrodes arranged in the V direction, it is possible to detect which location the external object is closer to in the H-V plane view in more detail.

In the display device 100A, an area corresponding to one of the partial detection areas A1, A2, A3, and A4 where the external object is closest to, can be set as an ultraviolet light emission target.

Figure 9:
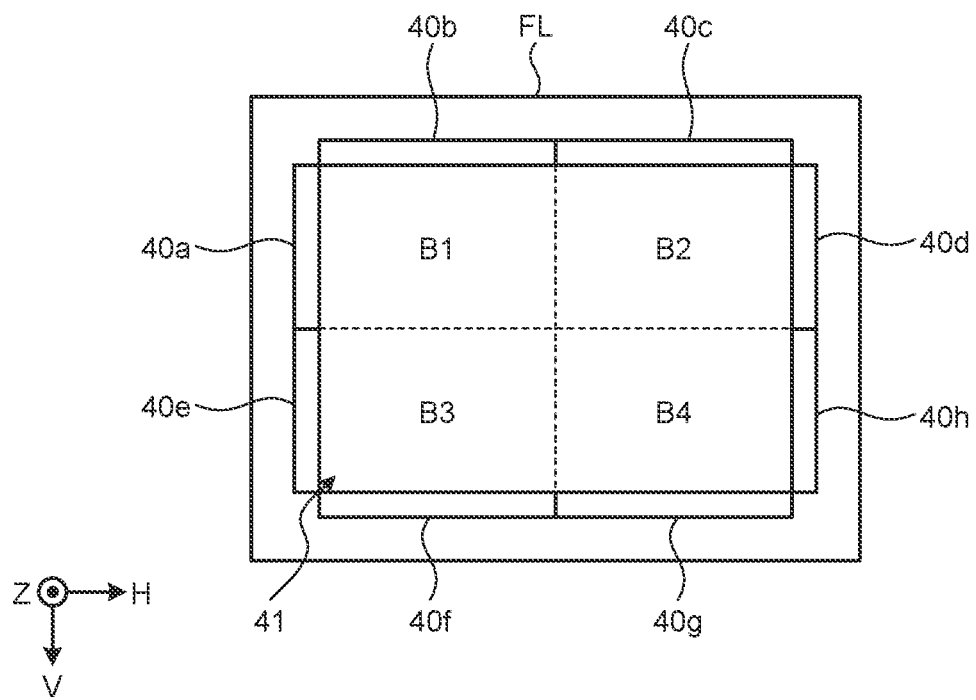
FIG. 9 is a plan view illustrating an example of an arrangement of a plurality of ultraviolet light emitters provided so as to emit ultraviolet light to an area closer to the partial detection area where an external object has been detected.

FIG. 9 is a plan view illustrating an example of an arrangement of a plurality of ultraviolet light emitters 40a, 40b, 40c, 40d, 40e, 40f, 40g, and 40h provided so as to emit ultraviolet light to an area closer to the partial detection area where an external object has been detected. Each of the ultraviolet light emitters 40a, 40b, 40c, 40d, 40e, 40f, 40g, and 40h has the same functional configuration as that of the ultraviolet light emitter 40.

As illustrated in FIG. 9, the ultraviolet light emitter 40a and the ultraviolet light emitter 40e, which are provided along one side in the V direction of the four sides of the rectangular light guide plate 41 in the H-V view, are arranged in the V direction. The lengths of the ultraviolet light emitter 40a and the ultraviolet light emitter 40e in the V direction are the same. The position of the ultraviolet light emitter 40a in the Z direction is located on the rear surface side of the detection electrode 51a. The position of the ultraviolet light emitter 40e in the Z direction is located on the rear surface side of the detection electrode 51b.

The ultraviolet light emitter 40d and the ultraviolet light emitter 40h, which are provided along the other side in the V direction of the four sides of the light guide plate 41, are arranged in the V direction. The lengths of the ultraviolet light emitter 40d and the ultraviolet light emitter 40h in the V direction are the same. The position of the ultraviolet light emitter 40d in the Z direction is located on the rear surface side of the detection electrode 53a. The position of the ultraviolet light emitter 40h in the Z direction is located on the rear surface side of the detection electrode 53b.

The ultraviolet light emitter 40b and the ultraviolet light emitter 40c, which are provided along one side in the H direction of the four sides of the light guide plate 41, are arranged in the H direction. The lengths of the ultraviolet light emitter 40b and the ultraviolet light emitter 40c in the H direction are the same. The position of the ultraviolet light emitter 40b in the Z direction is located on the rear surface side of the detection electrode 52a. The position of the ultraviolet light emitter 40c in the Z direction is located on the rear surface side of the detection electrode 52b.

The ultraviolet light emitter 40f and the ultraviolet light emitter 40g, which are provided along the other side in the H direction of the four sides of the light guide plate 41, are arranged in the H direction. The lengths of the ultraviolet light emitter 40f and the ultraviolet light emitter 40g in the H direction are the same. The position of the ultraviolet light emitter 40f in the Z direction is located on the rear surface side of the detection electrode 54a. The position of the ultraviolet light emitter 40g in the Z direction is located on the rear surface side of the detection electrode 54b.

It is possible to assume that the light guide plate 41 includes partial areas B1, B2, B3, and B4 provided in the locations overlapping with the partial detection areas A1, A2, A3, and A4 described with reference to FIG. 8, when viewed in the Z direction. The partial area B1 overlaps with the partial detection area A1. The ultraviolet light emitter 40a is placed along one of the four sides of the partial area B1, and the ultraviolet light emitter 40b is placed along another side, which is orthogonal to the one side. The partial area B2 overlaps with the partial detection area A2. The ultraviolet light emitter 40c is placed along one of the four sides of the partial area B2, and the ultraviolet light emitter 40d is placed along another side, which is orthogonal to the one side. The partial area B3 overlaps with the partial detection area A3. The ultraviolet light emitter 40e is placed along one of the four sides of the partial area B3, and the ultraviolet light emitter 40f is placed along another side, which is orthogonal to the one side. The partial area B4 overlaps with the partial detection area A4. The ultraviolet light emitter 40g is placed along one of the four sides of the partial area B4, and the ultraviolet light emitter 40h is placed along another side, which is orthogonal to the one side.

The controller 60 controls to turn ON ultraviolet light emitters of the ultraviolet light emitters 40a, 40b, 40c, 40d, 40e, 40f, 40g, and 40h, in accordance with which of the partial detection areas A1, A2, A3, and A4 an external object is in contact with or closest to.

For example, when the external object is in contact with or closest to the partial detection area A1, the controller 60 turns ON the ultraviolet light emitters 40a and 40b. Consequently, ultraviolet light is emitted to the partial detection area A1 from the partial area B1. That is, in this case, the partial detection area A1 that the external object is in contact with or closest to can be set as an ultraviolet light emission target. In this manner, the display surface side of the partial detection area A1 that the external object is in contact with or closest to can be more effectively sterilized.

When the external object is in contact with or closest to the partial detection area A2, the controller 60 turns ON the ultraviolet light emitters 40c and 40d. Consequently, ultraviolet light is emitted to the partial detection area A2 from the partial area B2. When the external object is in contact with or closest to the partial detection area A3, the controller 60 turns ON the ultraviolet light emitters 40e and 40f. Consequently, ultraviolet light is emitted to the partial detection area A3 from the partial area B3. When the external object is in contact with or closest to the partial detection area A4, the controller 60 turns ON the ultraviolet light emitters 40g and 40h. Consequently, ultraviolet light is emitted to the partial detection area A4 from the partial area B4. In these manners, the partial detection area that the external object is in contact with or closest to can be set as an ultraviolet light emission target. Thus, the display surface side of the partial detection area in contact with or closest to the external object can be more effectively sterilized.

Figure 10:
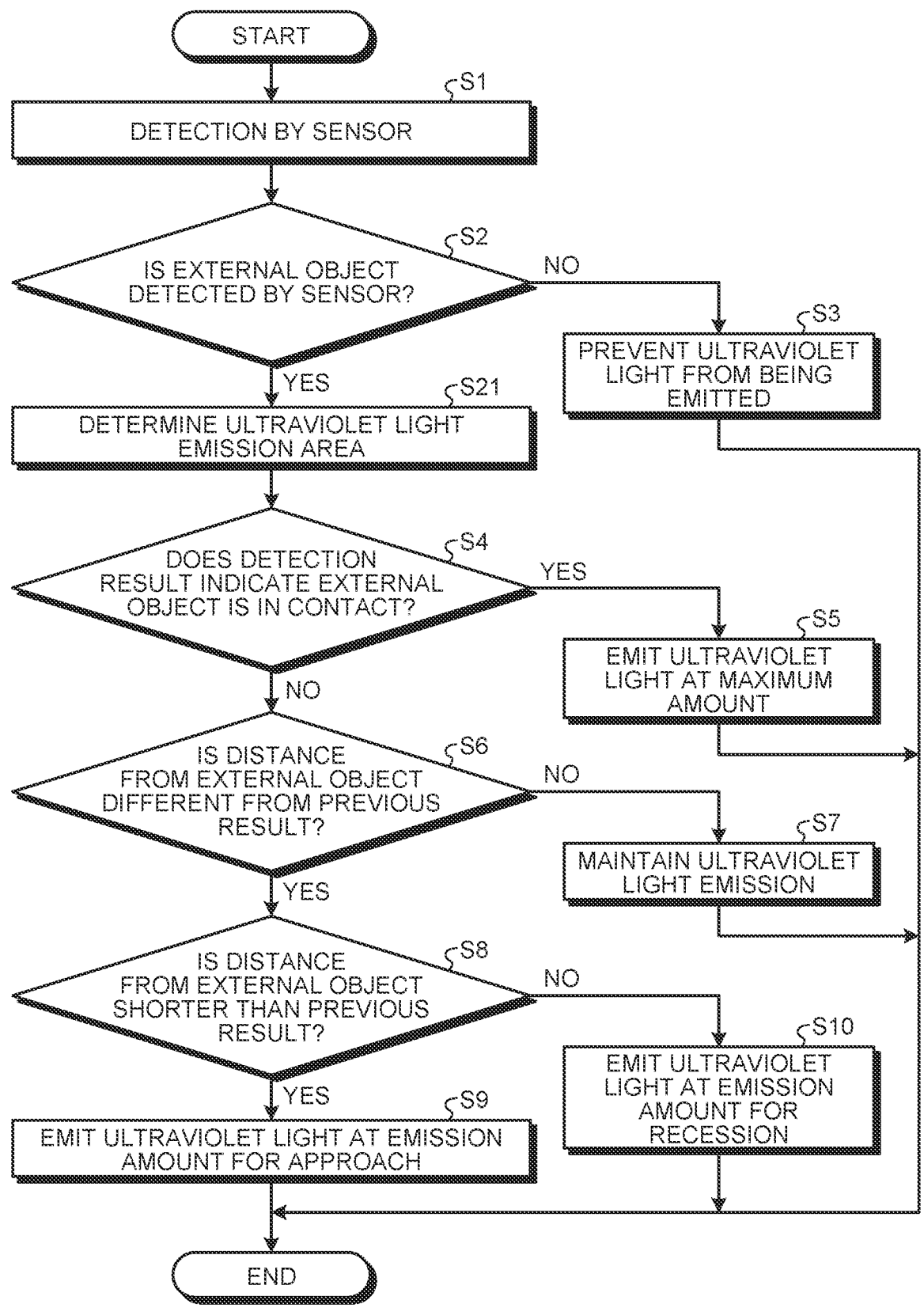
FIG. 10 is a flowchart illustrating a process performed by a controller in a first modification.

FIG. 10 is a flowchart illustrating a process performed by the controller 60 in the first modification. In the first modification, a determination process of an ultraviolet emission area (step S21) is performed prior to the determination process at step S4, which is performed after "the external object is detected in the process at step S1 (Yes at step S2)" is determined in the determination process at step S2. In the process at step S21, the controller 60 controls to turn ON ultraviolet light emitters among the ultraviolet light emitters 40a, 40b, 40c, 40d, 40e, 40f, 40g, and 40h so as to cause ultraviolet light to be emitted to the partial detection area where the external object is in contact or is closest. For example, when the external object is in contact with or closest to the partial detection area A1, the controller 60 turns ON the ultraviolet light emitters 40a and 40b.

As described above, the first modification is described assuming that the partial detection areas A1, A2, A3, and A4, and the partial areas B1, B2, B3, and B4 are arranged in a two-by-two arrangement in the H direction and the V direction. However, the arrangement of the partial detection areas and the partial areas overlapping with the partial detection areas is not limited to the two-by-two arrangement. For example, by dividing the detection electrodes 51 and 53 illustrated in FIG. 2 into three or more, the number of the partial detection areas arranged in the V direction can be three or more. By dividing the detection electrodes 52 and 54 illustrated in FIG. 2 into three or more, the number of the partial detection areas arranged in the H direction can be three or more. By providing a plurality of the ultraviolet light emitters 40 individually overlapping with the electrodes divided into three or more, it is possible to easily and individually emit ultraviolet light to the partial detection areas.

For example, when the partial detection areas are arranged in a three-by-three arrangement in the H direction and the V direction, the center partial detection area will not have any ultraviolet light emitters 40 arranged adjacent thereto. In this case, by turning ON one or more ultraviolet light emitters 40 closer to the center partial detection area, the center partial detection area can be more effectively sterilized. More specifically, two ultraviolet light emitters 40 that face each other in the V direction with the center partial detection area interposed therebetween may be turned ON. When there are α×β partial detection areas in the H direction and the V direction, the same idea as that for the above-mentioned center partial detection area may be applicable to the partial detection area that is not in contact with the outer periphery of the display area AA. α and β are both natural numbers of three or more.

As described above, according to the first modification, ultraviolet light is emitted to a part of the display surface to or with which the external object is closer or in contact. In this manner, it is possible to emit ultraviolet light only to a portion where pathogens may be transmitted from the external object and to portions around the portion. Thus, sterilization can be performed more effectively with less power consumption.

As illustrated in FIG. 1, the sterilization device 1 may further include a visible light emitter 35. The visible light emitter 35 includes a light source (visible light source) that emits visible light VL (see FIG. 11). Hereinafter, unless otherwise specified, when a visible light source is simply referred to without a reference numeral, it denotes the visible light source provided in the visible light emitter 35. The visible light source is an LED, for example. However, it is not limited thereto and may be any light emitting element and the like that emits visible light in accordance with the power supply. When the display panel P is an image display panel of a self-light emission type, the visible light emitter 35 will be omitted. For example, the image display panel of a self-light emission type includes an organic light emitting diode (OLED) panel. In the first embodiment and the modification, the image display panel of a self-light emission type is employed as the display panel P.

Second Embodiment

In the second embodiment, a liquid crystal display panel that requires an external light source for emitting the visible light VL is employed, instead of the display panel P in the first embodiment. For example, the visible light emitter 35 that functions as such an external light source is provided as a front light that illuminates a reflective liquid crystal display panel PA illustrated in FIG. 11, which will be described later. The following describes the display device 100A of the second embodiment in which the display panel P of the first embodiment is employed as the reflective liquid crystal display panel PA, with reference to FIG. 11 and FIG. 12.

Figure 11:
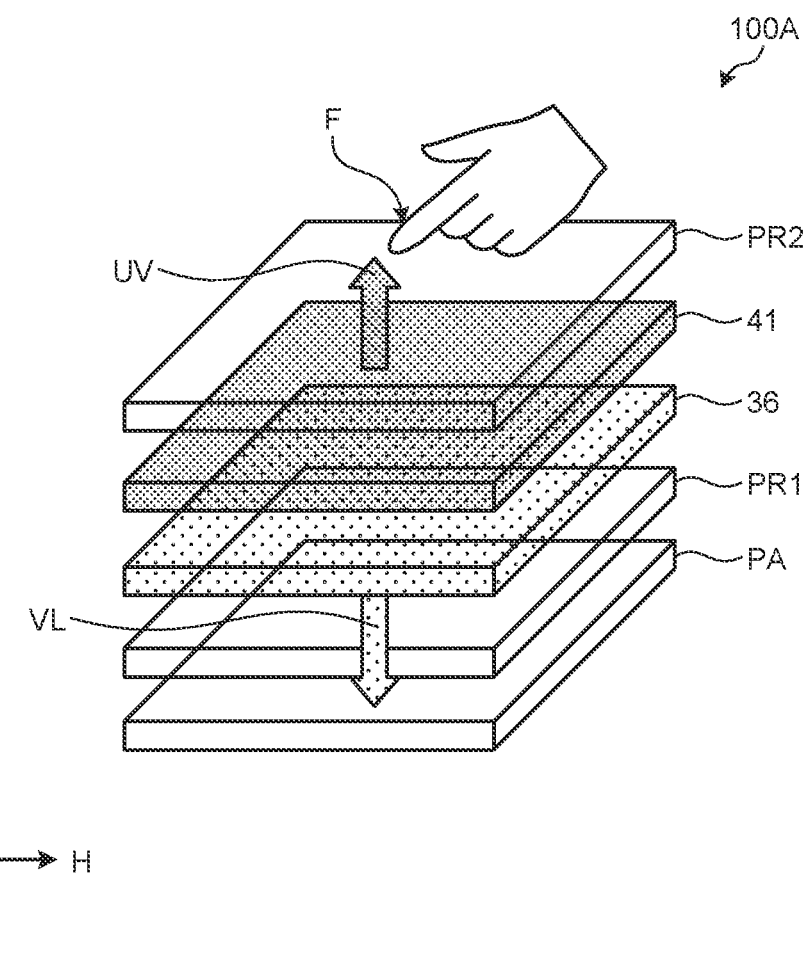
FIG. 11 is a conceptual diagram illustrating the order of layering the main components of a display device in a second embodiment.

FIG. 11 is a conceptual diagram illustrating the order of layering the main components of the display device 100A in the second embodiment. In the display device 100A, a light guide plate 36 is provided between the protection layer PR1 and the light guide plate 41 of the display device 100 described with reference to FIG. 4.

Figure 12:
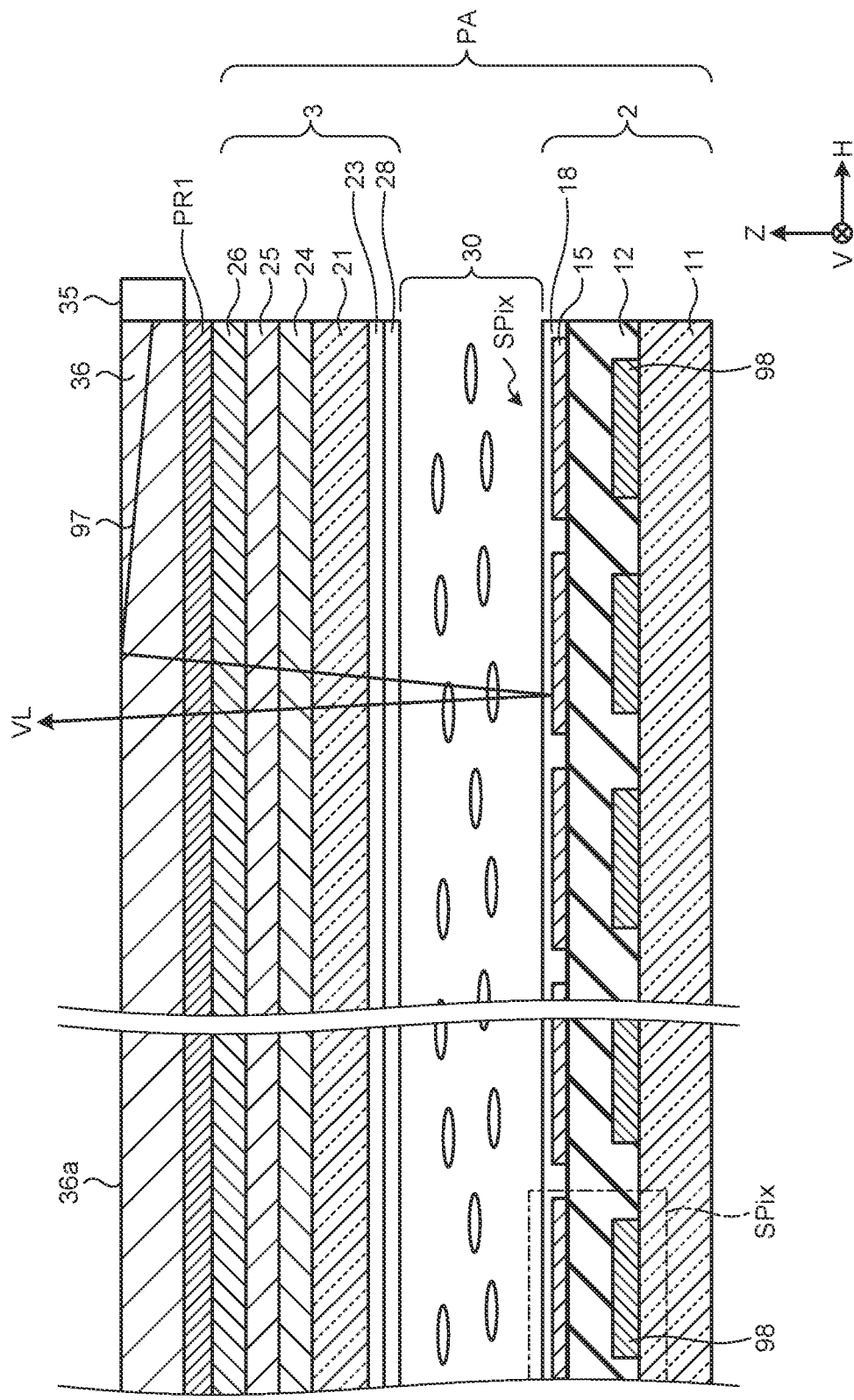
FIG. 12 is a schematic diagram illustrating an example of a layer structure of a liquid crystal display panel, a protection layer, and a visible light emitter, and an example of a main configuration of the display panel.

FIG. 12 is a schematic diagram illustrating an example of a layer structure of the liquid crystal display panel PA, the protection layer PR1, and the visible light emitter 35, and an example of a main configuration of the liquid crystal display panel PA. As illustrated in FIG. 12, the liquid crystal display panel PA includes a first panel 2, a second panel 3, and a liquid crystal layer 30. The liquid crystal display panel PA is stacked so as to face the light guide plate 36 with the protection layer PR1 interposed therebetween. The light guide plate 36 is a visible light guide plate having a rectangular shape with the same size as that of the light guide plate 41 in the H-V view. The visible light emitter 35 is provided on the lateral side of the light guide plate 36. In FIG. 12, the visible light emitter 35 is adjacent to the light guide plate 36 in the H direction. However, it is not limited thereto. For example, the visible light emitter 35 may be adjacent to the light guide plate 36 in the V direction. A plurality of visible light emitting sources such as visible light sources 35a, 35b, 35c, 35d, 35e, 35f, 35g, and 35h illustrated in FIG. 13, which will be described later, may be provided.

The second panel 3 is disposed opposite to the first panel 2. The light guide plate 36 is laminated on the main surface of the second panel 3 in the Z direction. The liquid crystal layer 30 is provided between the first panel 2 and the second panel 3.

In a period during which the visible light emitter 35 does not emit the visible light VL, the light entered from the outside on the display surface side is reflected by a pixel electrode (reflective electrode) 15 of the first panel 2 and is emitted from the display surface. The liquid crystal display panel PA uses the visible light included in the reflected light to display an image on the display surface side.

In a period during which the visible light emitter 35 emits the visible light VL, the visible light VL that has entered into the side surface of the light guide plate 36 from the visible light emitter 35, is reflected in a direction opposite to the Z direction by a surface 36a on an opposite side to the protection layer PR1 side. The visible light VL is then reflected by the pixel electrode 15 and is emitted from the display surface. Although not illustrated in FIG. 12, as illustrated in FIG. 11, the light guide plate 41 is stacked on the display surface side that is the opposite side to the protection layer PR1 side with the light guide plate 36 interposed therebetween. The configuration on the light guide plate 41 side above the light guide plate 36 is the same as the configuration on the light guide plate 41 side illustrated in FIG. 4.

The first panel 2 includes a first substrate 11, an insulating layer 12, the pixel electrode 15, and an orientation film 18. For example, the first substrate 11 is a glass substrate or a resin substrate. A circuit element and various types of wiring such as a gate line and a data line, which are not illustrated, are provided on the surface of the first substrate 11. The circuit element includes a switching element such as a thin film transistor (TFT) and a capacitance element.

The insulating layer 12 is provided on the first substrate 11 and flattens the surfaces of the circuit element and various types of wiring as a whole. A plurality of the pixel electrodes 15 are provided on the insulating layer 12. The orientation film 18 is provided between the pixel electrodes 15 and the liquid crystal layer 30. The rectangular-shaped pixel electrode 15 is provided for each pixel SPix. For example, the pixel electrode 15 is formed of metal such as aluminum (Al) or silver (Ag). The pixel electrode 15 may be configured by layering the above-described metal material and a light-transmitting conductive material such as indium tin oxide (ITO). A material with a favorable reflectivity is used for the pixel electrode 15, and the pixel electrode 15 functions as a reflective plate that diffuses and reflects the light entering from the outside.

The light (for example, the visible light VL) reflected by the pixel electrode 15 is scattered by diffuse reflection, but travels in a uniform direction toward the display surface side. When the voltage level applied to the pixel electrode 15 is changed, the transmission state of light through the liquid crystal layer 30 on the pixel electrode 15, that is, the transmission state of the reflected light of each pixel SPix is changed.

The second panel 3 includes a second substrate 21, a common electrode 23, an orientation film 28, a ¼ wavelength plate 24, a ½ wavelength plate 25, and a polarizing plate 26. Of the two surfaces of the second substrate 21, the common electrode 23 is provided on a surface facing the first panel 2. The orientation film 28 is provided between the common electrode 23 and the liquid crystal layer 30. On the surface on the display surface side of the second substrate 21, the ¼ wavelength plate 24, the ½ wavelength plate 25, and the polarizing plate 26 are layered in the order as listed.

For example, the second substrate 21 is a glass substrate or a resin substrate. The common electrode 23 is formed of a light-transmitting conductive material such as ITO. The common electrode 23 is disposed opposite to the pixel electrodes 15 and supplies a common potential to each pixel SPix.

For example, the liquid crystal layer 30 includes a nematic liquid crystal. When the voltage level between the common electrode 23 and the pixel electrode 15 is changed, the orientation of liquid crystal molecules in the liquid crystal layer 30 is changed. In this manner, the light that transmits through the liquid crystal layer 30 is modulated for each pixel SPix.

The natural light or the visible light VL becomes incident light that enters from the display surface side of the liquid crystal display panel PA, transmits through the second panel 3 and the liquid crystal layer 30, and reaches the pixel electrode 15. The incident light is reflected by the pixel electrode 15 of each pixel SPix. Such reflected light is modulated for each pixel SPix and is emitted from the display surface. In this manner, an image is displayed.

In the reflective liquid crystal display, a memory that holds the potential to be applied to each pixel SPix may be provided for each pixel SPix. In this case, the memory is provided on a backplane 98.

As described above, unless otherwise specifically described, the second embodiment is the same as the first embodiment. According to the second embodiment, the liquid crystal display panel PA is a reflective liquid crystal display panel and includes the visible light emitter 35 that functions as a front light for emitting visible light to the liquid crystal display panel PA. In this manner, the display device 100A including the reflective liquid crystal display panel can also increase and decrease the emission amount of ultraviolet light.

Second Modification

Next, a second modification in which the liquid crystal display panel PA is applied to the above-described first modification will be described with reference to FIG. 13 to FIG. 17. In the second modification, the same reference numerals denote the same components as those in the first modification, and the duplicate description thereof may be omitted.

Figure 13:
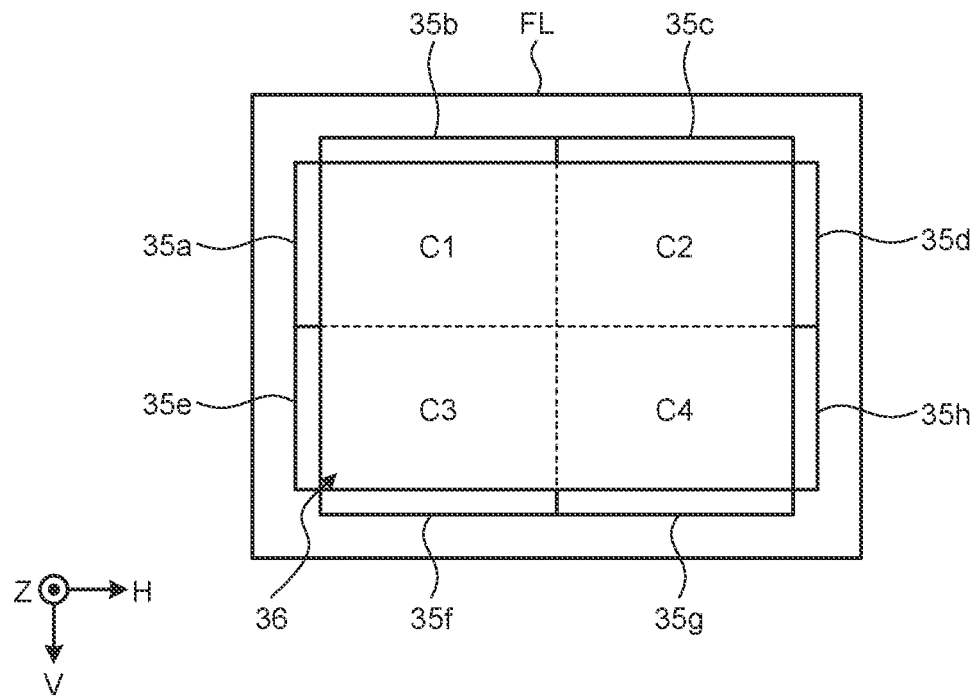
FIG. 13 is a plan view illustrating an example of a positional relation between visible light sources and a light guide plate.

FIG. 13 is a plan view illustrating an example of a positional relation between the visible light sources 35a, 35b, 35c, 35d, 35e, 35f, 35g, and 35h, and the light guide plate 36. The visible light sources 35a, 35b, 35c, 35d, 35e, 35f, 35g, and 35h illustrated in FIG. 13 are included in the visible light emitter 35 illustrated in FIG. 1.

As illustrated in FIG. 13, the visible light source 35a and the visible light source 35e, which are provided along one side in the V direction of the four sides of the rectangular light guide plate 36 in the H-V view, are arranged in the V direction. The lengths of the visible light source 35a and the visible light source 35e in the V direction are the same. The position of the visible light source 35a in the Z direction is located on the rear surface side of the ultraviolet light emitter 40a illustrated in FIG. 9. The position of the visible light source 35e in the Z direction is located on the rear surface side of the ultraviolet light emitter 40e illustrated in FIG. 9.

The visible light source 35d and the visible light source 35h, which are provided along the other side in the V direction of the four sides of the light guide plate 36, are arranged in the V direction. The lengths of the visible light source 35d and the visible light source 35h in the V direction are the same. The position of the visible light source 35d in the Z direction is located on the rear surface side of the ultraviolet light emitter 40d illustrated in FIG. 9. The position of the visible light source 35h in the Z direction is located on the rear surface side of the ultraviolet light emitter 40h illustrated in FIG. 9.

The visible light source 35b and the visible light source 35c, which are provided along one side in the H direction of the four sides of the light guide plate 36, are arranged in the H direction. The lengths of the visible light source 35b and the visible light source 35c in the H direction are the same. The position of the visible light source 35b in the Z direction illustrated in FIG. 9 is located on the rear surface side of the ultraviolet light emitter 40b illustrated in FIG. 9. The position of the visible light source 35c in the Z direction is located on the rear surface side of the ultraviolet light emitter 40c illustrated in FIG. 9.

The visible light source 35f and the visible light source 35g, which are provided along the other side in the H direction of the four sides of the light guide plate 36, are arranged in the H direction. The lengths of the visible light source 35f and the visible light source 35g in the H direction are the same. The position of the visible light source 35f in the Z direction is located on the rear surface side of the ultraviolet light emitter 40f illustrated in FIG. 9. The position of the visible light source 35g in the Z direction is located on the rear surface side of the ultraviolet light emitter 40g illustrated in FIG. 9.

It is possible to assume that the light guide plate 36 includes visible light emitting areas C1, C2, C3, and C4 provided on the locations overlapping with the partial detection areas A1, A2, A3, and A4 described with reference to FIG. 8, when viewed in the Z direction. The visible light emitting area C1 overlaps with the partial detection area A1. The visible light source 35a is placed along one of the four sides of the visible light emitting area C1, and the visible light source 35b is placed along another side, which is orthogonal to the one side. The visible light emitting area C2 overlaps with the partial detection area A2. The visible light source 35c is placed along one of the four sides of the visible light emitting area C2, and the visible light source 35d is placed along another side, which is orthogonal to the one side. The visible light emitting area C3 overlaps with the partial detection area A3. The visible light source 35e is placed along one of the four sides of the visible light emitting area C3, and the visible light source 35f is placed along another side, which is orthogonal to the one side. The visible light emitting area C4 overlaps with the partial detection area A4. The visible light source 35g is placed along one of the four sides of the visible light emitting area C4, and the visible light source 35h is placed along another side, which is orthogonal to the one side.

Figure 14:
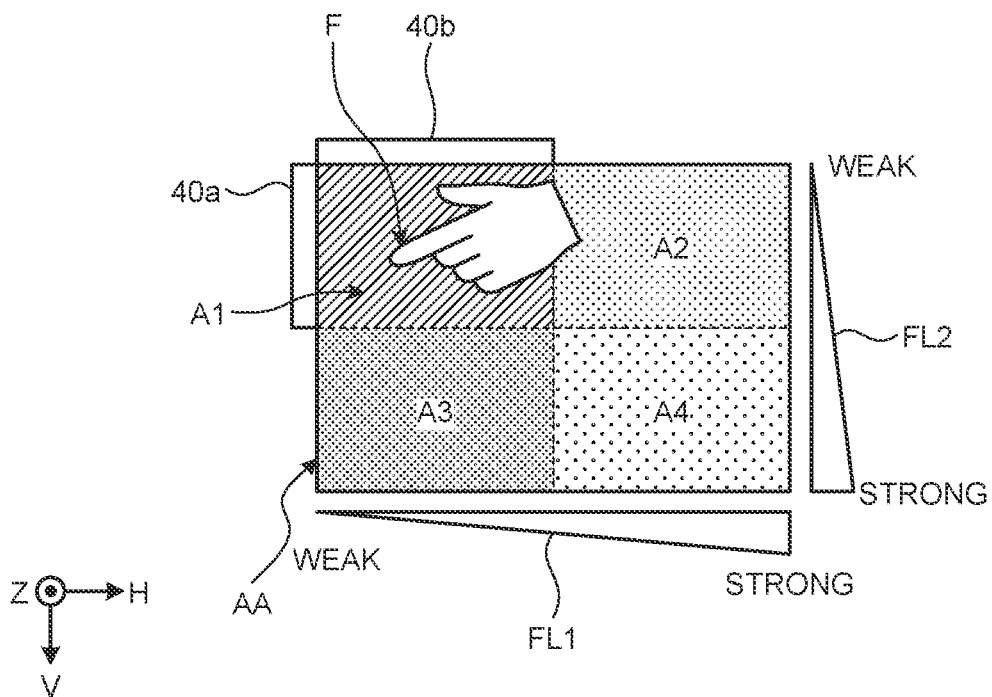
FIG. 14 is a schematic diagram illustrating an example of a relation between the ultraviolet light emission control and the visible light emission control in a second modification.

FIG. 14 is a schematic diagram illustrating an example of a relation between the ultraviolet light emission control and the visible light VL emission control in the second modification. In the example illustrated in FIG. 14, the finger F is closest to the partial detection area A1. Consequently, as is the case with the first modification, the controller 60 turns ON the ultraviolet light emitters 40a and 40b to emit ultraviolet light to the partial detection area A1.

The controller 60 of the second modification also controls the lighting of the visible light sources (for example, the visible light sources 35a, 35b, . . . , 35h) such that the amount of visible light VL emitted from the visible light emitter 35 to the partial detection area (in the example of FIG. 14, the partial detection area A1) serving as an ultraviolet light emission target, becomes smaller than those of the other partial detection areas.

As illustrated in FIG. 14, when the partial detection area A1 serves as an ultraviolet light emission target, among the visible light sources 35a, 35b, . . . , 35h illustrated in FIG. 13, the controller 60 sets the emission amount of visible light VL from the visible light sources 35a and 35b adjacent to the visible light emitting area C1, which overlaps with the partial detection area A1 in the Z direction, at an amount less than the emission amount of visible light VL from the other visible light sources 35c, 35d, 35e, 35f, 35g, and 35h. In this manner, the emission amount of visible light VL from the visible light emitter 35 to the partial detection area A1 becomes less than those to the partial detection areas A2, A3, and A4.

Any specific method for controlling the emission amount of visible light VL from the visible light emitter 35 can be employed. For example, the emission amount of visible light VL from the visible light emitter 35 may be controlled, by controlling the length of light emission time of the visible light source per unit time, by controlling the light emission intensity of the visible light source provided such that the light emission intensity is controllable, or by a combination of the two methods.

Because a hand of a user including the finger F is placed in the partial detection area A1, the visibility of an image is not regarded important in the partial detection area A1, compared with the partial detection areas A2, A3, and A4. Consequently, the power consumption can be reduced by reducing the amount of visible light VL to be emitted to the partial detection area A1. On the other hand, because an external object such as the finger F may be in contact with the partial detection area A1, the display surface side of the partial detection area A1 may need to be sterilized. Hence, as is the case with the first modification, the controller 60 turns ON the ultraviolet light emitters 40a and 40b to emit ultraviolet light to the partial detection area A1.

In the example illustrated in FIG. 14, the emission amount of visible light VL from the visible light sources 35a and 35b is caused to be less than the emission amount of visible light VL from the other visible light sources 35c, 35d, 35e, 35f, 35g, and 35h. Hence, the partial detection area A1 becomes relatively darker than the other partial detection areas. Compared to the partial detection area A2 adjacent to the partial detection area A1 in the H direction and the partial detection area A3 adjacent to the partial detection area A1 in the V direction, the partial detection area A4 not adjacent to the partial detection area A1 in the H direction nor the V direction becomes brighter than the partial detection area A2 and the partial detection area A3. Thus, in the example illustrated in FIG. 14, as illustrated in a luminance graph FL1 in the H direction, the partial detection areas A2 and A4 look brighter than the partial detection areas A1 and A3. In the example illustrated in FIG. 14, as illustrated in a luminance graph FL2 in the V direction, the partial detection areas A3 and A4 look brighter than the partial detection areas A1 and A2. In FIG. 14, a relative difference of brightness in the partial detection areas A1, A2, A3, and A4 is schematically illustrated by the density of dot patterns. The brightness is increased as the dots become more spaced.

As described above, as illustrated in FIG. 13, the second modification is described assuming that the visible light emitting areas C1, C2, C3, and C4 are arranged in a two-by-two arrangement in the H direction and the V direction. However, the emission amount of visible light VL may be controlled in other ways. For example, the number of the visible light sources arranged in the H direction may be three or more, and the number of the visible light sources arranged in the V direction may be three or more.

For example, when the visible light sources are arranged in a three-by-three arrangement in the H direction and the V direction, the center partial detection area will not have any visible light sources arranged adjacent thereto. In this case, by relatively reducing the emission amount of visible light VL from at least one visible light source closer to the center partial detection area, the center partial detection area can be made relatively darker than the other partial detection areas. More specifically, the emission amount of visible light VL from two visible light sources that face each other in the V direction with the center partial detection area interposed therebetween may be relatively reduced. The emission amount of visible light VL from two visible light sources that face each other in the H direction with the center partial detection area interposed therebetween may be relatively reduced. When there are γ×Δ partial detection areas in the H direction and the V direction, the same idea as that for the above-mentioned center partial detection area may be applicable to the partial detection area that is not in contact with the outer periphery of the display area AA. γ and Δ are both natural numbers of three or more.

Figure 15:
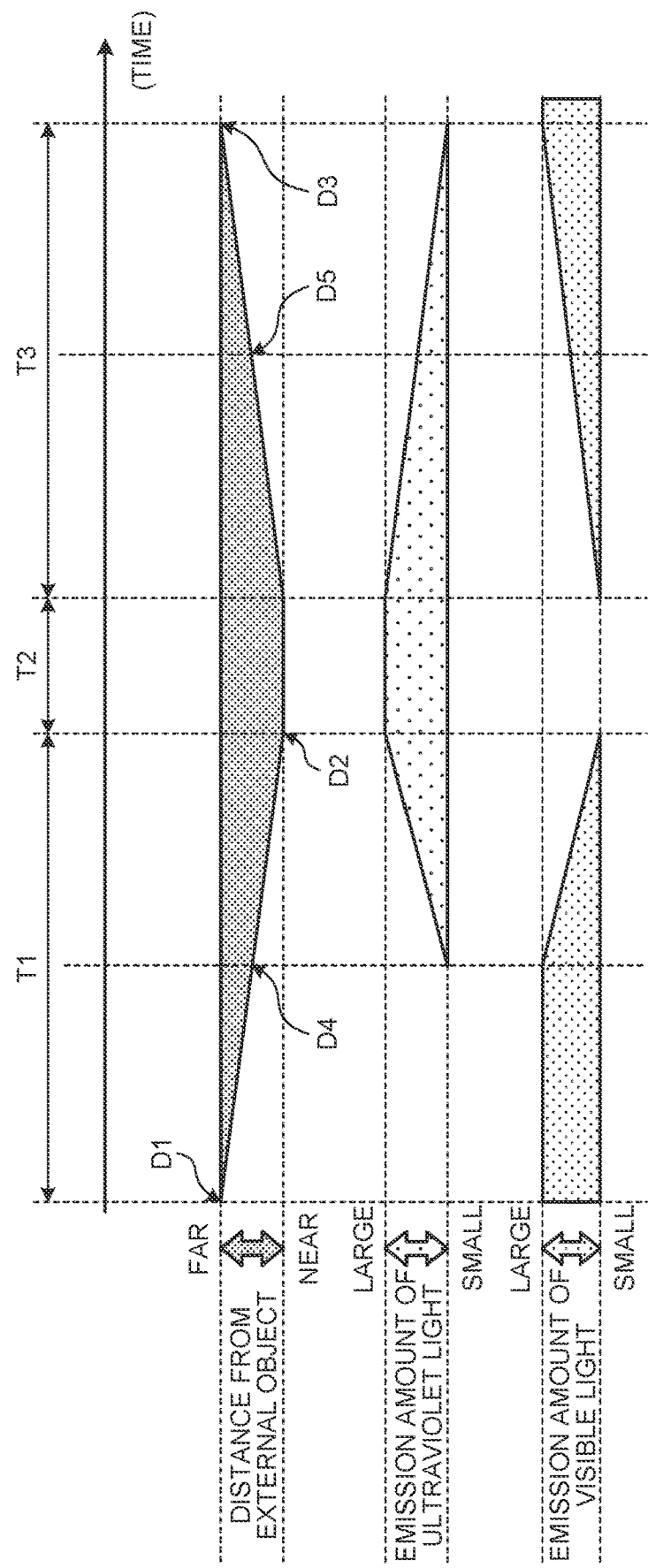
FIG. 15 is a time chart illustrating an example of a relation of the distance between a partial detection area serving as a ultraviolet light emission target and an external object, the amount of ultraviolet light to be emitted to the partial detection area, and the amount of visible light to be emitted to the partial detection area by a visible light emitter.

FIG. 15 is a time chart illustrating an example of a relation of the distance between a partial detection area serving as an ultraviolet light emission target and an external object, the emission amount of ultraviolet light from the ultraviolet light emitter 40 that emits ultraviolet light to the partial detection area, and the a emission mount of visible light VL from a visible light source that emits the visible light VL to the partial detection area. The relation of the distance between the partial detection area serving as an ultraviolet light emission target and the external object, and the emission amount of ultraviolet light from the ultraviolet light emitter 40 that emits ultraviolet light to the partial detection area in FIG. 15, is the same as that described with reference to FIG. 6. Thus, also in the description with reference to FIG. 15, the expressions of "A: approaching" and "B: receding" described above will be used.

As illustrated in FIG. 15, when an external object is "A: approaching" during period T1, the controller 60 does not reduce the emission amount of visible light VL from the visible light source, until the distance between the display device 100 and the external object reaches distance D4. In this example, "does not reduce the emission amount of visible light VL" refers to a state where the controller 60 operates the visible light source such that an amount of visible light VL required for display output of a normal image is supplied.

When the external object is "A: approaching" during period T1, the controller 60 controls the visible light emitter 35 such that the emission amount of visible light VL from the visible light source is reduced as the distance between the display device 100 and the external object decreases from distance D4 to distance D2. While the distance between the display device 100 and the external object is kept at distance D2 during period T2, the controller 60 controls the visible light emitter 35 such that the emission amount of visible light VL from the visible light source is kept low. In FIG. 15, the emission amount of visible light VL during period T2 is zero. However, it is not limited thereto, and the visible light VL may be emitted to a certain degree. When the external object is "B: receding" during period T3, the controller 60 controls the visible light emitter 35 such that the emission amount of visible light VL from the visible light source is increased as the distance between the display device 100 and the external object is increased from distance D2 via distance D5 to distance D3.

As illustrated in FIG. 15, the emission amount of visible light VL corresponding to distance D5 when the external object is "B: receding", is less than the emission amount of visible light VL corresponding to distance D4 when the external object is "A: approaching". This is because the emission amount of visible light VL is controlled in an opposite manner to the control of the emission amount of ultraviolet light.

Figure 16:
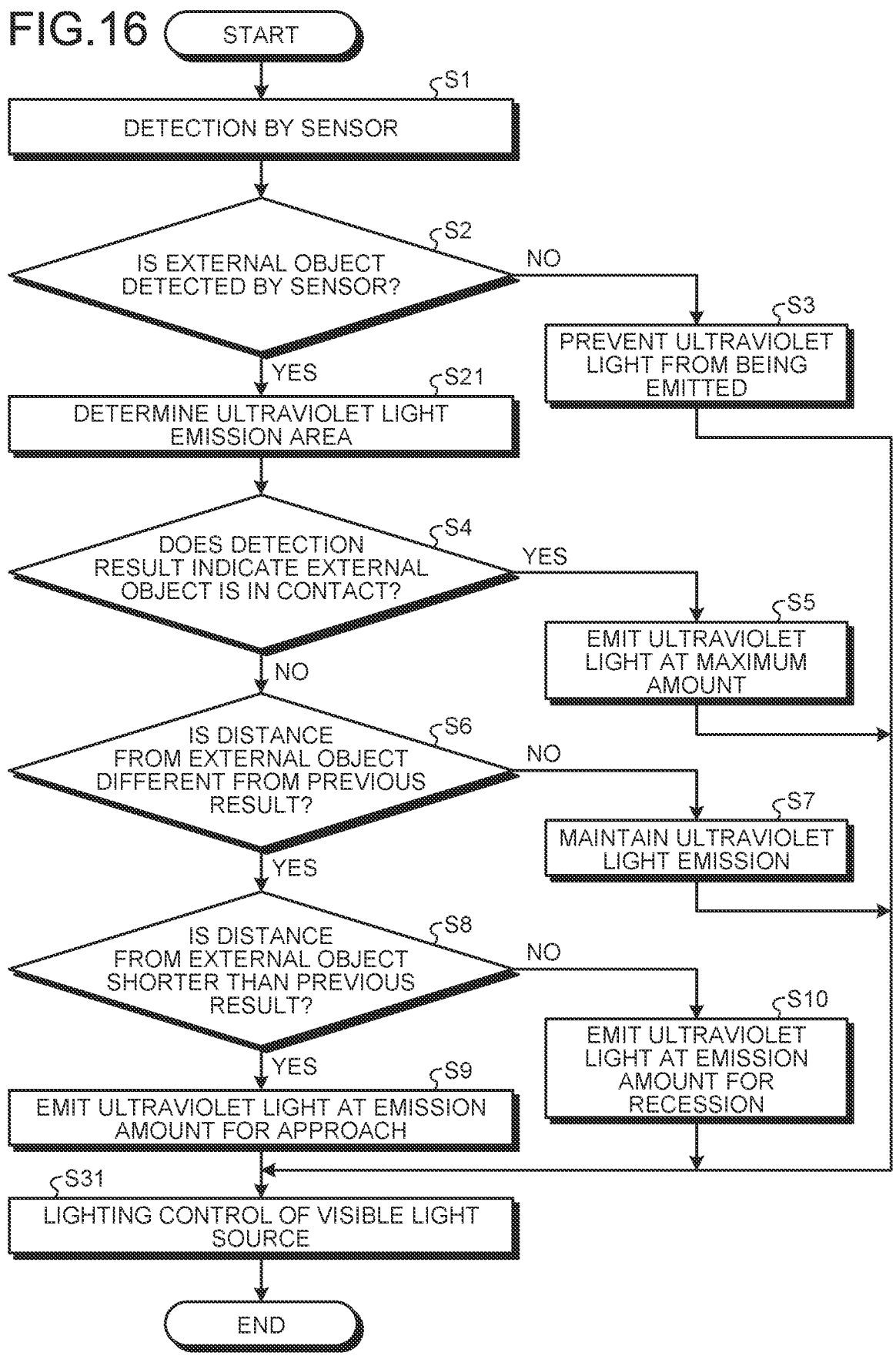
FIG. 16 is a flowchart illustrating a process performed by a controller in the second modification.

FIG. 16 is a flowchart illustrating a process performed by the controller 60 in the second modification. In the second modification, in addition to the process performed by the controller 60 in the first modification described with reference to FIG. 10, the lighting control of the visible light source (step S31) is performed after the process at step S3, step S5, step S7, step S9, or step S10. In the process at step S31, the emission amount control of visible light VL is performed on the visible light source placed adjacent or closer to the partial detection area serving as the ultraviolet emission area determined at step S21. The emission amount control of visible light VL is performed such that the emission amount of visible light VL is controlled to be an amount obtained by reversing the increase or decrease in the amount of the ultraviolet light determined in the process at step S3, step S5, step S7, step S9, or step S10.

The arrangement of the sterilization lamps and the visible light sources in the H-V plane view is not limited to a combination of the arrangement of the ultraviolet light emitters 40a, 40b, 40c, 40d, 40e, 40f, 40g, and 40h illustrated in FIG. 9, and the arrangement of the visible light sources 35a, 35b, 35c, 35d, 35e, 35f, 35g, and 35h illustrated in FIG. 13.

Figure 17:
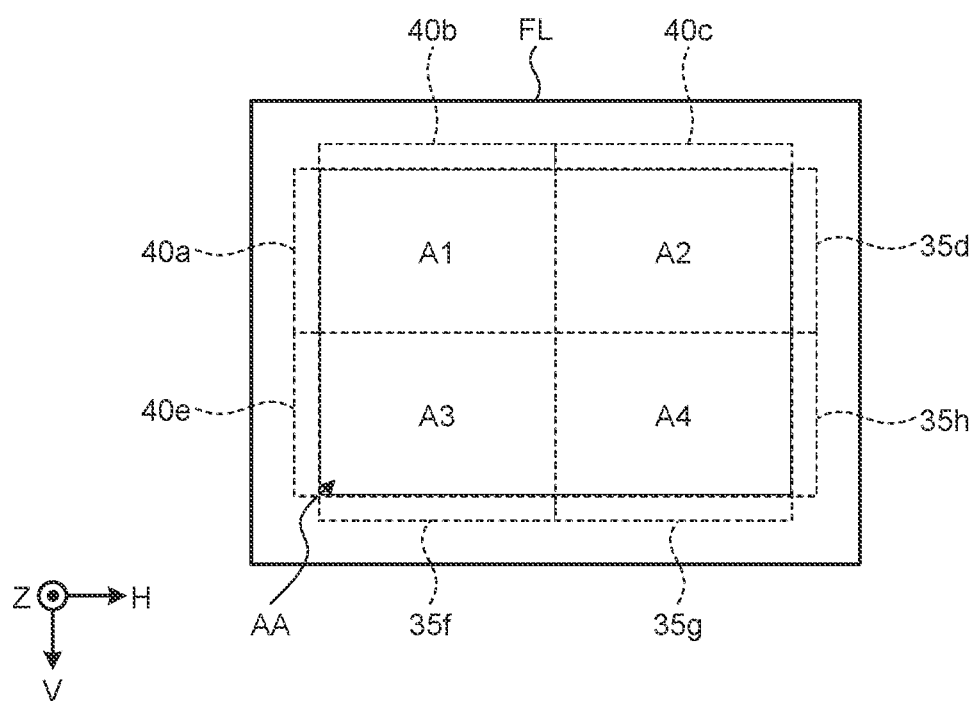
FIG. 17 is a plan view illustrating another example of an arrangement of sterilization lamps and visible light sources.

FIG. 17 is a plan view illustrating another example of the arrangement of the sterilization lamps and the visible light sources. As illustrated in FIG. 17, the sterilization lamps and the visible light sources may be disposed such that the sterilization lamps and the visible light sources do not overlap with each other in the H-V plane view. In the example illustrated in FIG. 17, the ultraviolet light emitters 40a, 40b, 40c, and 40e are disposed, among the ultraviolet light emitters 40a, 40b, 40c, 40d, 40e, 40f, 40g, and 40h illustrated in FIG. 9. In the example illustrated in FIG. 17, the visible light sources 35d, 35f, 35g, and 35h are disposed, among the visible light sources 35a, 35b, 35c, 35d, 35e, 35f, 35g, and 35h illustrated in FIG. 13.

As described above, according to the second modification, ultraviolet light is emitted to a part of the display surface to or with which the external object is closer or in contact, and the amount of visible light emitted to the part of the display surface is less than those of the other parts. In this manner, it is possible to reduce the power consumption for illuminating an area that the external object is in proximity to and that is considered the need for visible light is relatively low, and for illuminating the vicinity of the area. Thus, it is possible to further reduce the power consumption.

In the second modification, the visible light emitter 35 is what is called a front light. However, the visible light emitter 35 is not limited to what is called a front light. The liquid crystal display panel is not limited to the reflective type. With reference to FIG. 18 to FIG. 21, a third modification will be described in which a transmissive liquid crystal display panel PB that is illuminated by the visible light VL from a backlight BL is employed, instead of the liquid crystal display panel PA including the front light described with reference to FIG. 12.

Third Modification

FIG. 18 is a conceptual diagram illustrating the order of layering the main components of a display device 100B in the third modification. In the display device 100B, the backlight BL and the protection layer PR2 are provided with the liquid crystal display panel PB interposed therebetween; the backlight BL is provided on the rear surface side of the liquid crystal display panel PB, and the protection layer PR2 is provided on the display surface side of the liquid crystal display panel PB. The liquid crystal display panel PB illustrated in FIG. 18 is what is called an in-cell type touch panel in which a display DP that functions as a transmissive liquid crystal display panel and a sensor 50A that detects proximity or contact of an external object are integrally provided. In the third modification, the sensor 50A detects proximity or contact of an external object, instead of the sensor 50 described above.

Figure 19:
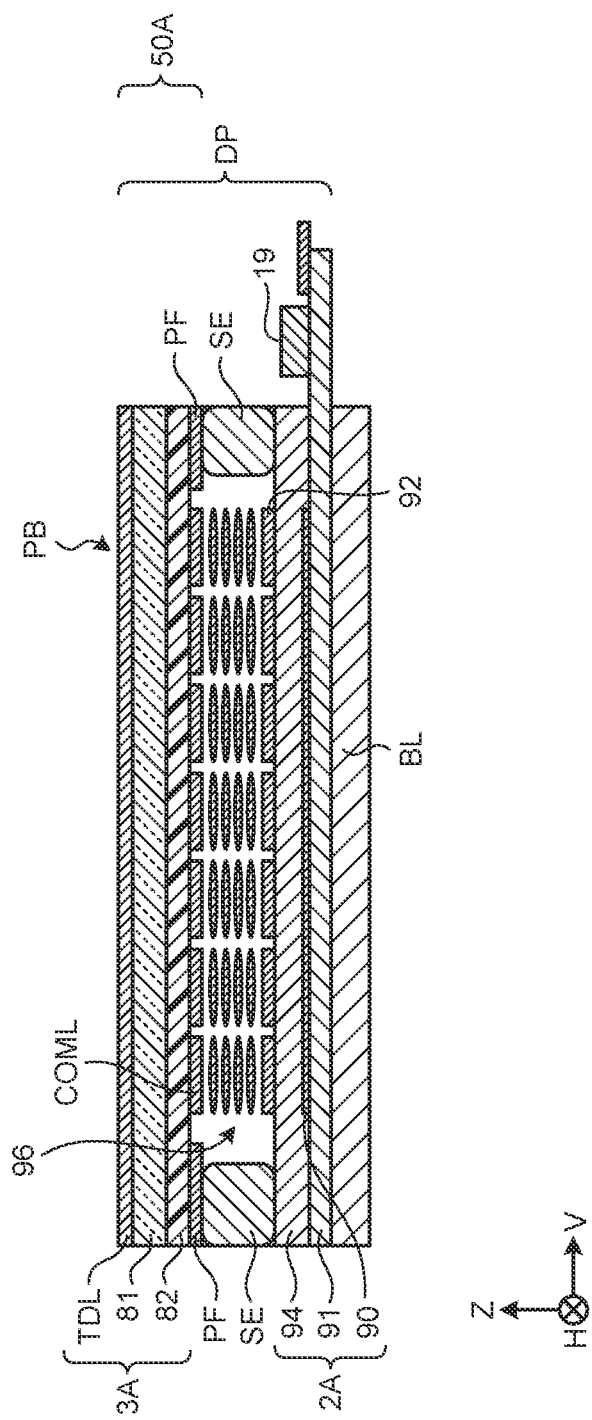
FIG. 19 is a sectional view illustrating a schematic sectional structure of the liquid crystal display panel.

FIG. 19 is a sectional view illustrating a schematic sectional structure of the liquid crystal display panel PB. The liquid crystal display panel PB includes a first substrate 2A, a second substrate 3A, and a liquid crystal layer 96. The first substrate 2A includes a glass substrate 91, an insulating layer 94, a circuit layer 90, and a plurality of pixel electrodes 92 disposed on the insulating layer 94 in a matrix (row-column configuration). The second substrate 3A includes a glass substrate 81, a color filter 82 formed on one surface of the glass substrate 81, and a plurality of drive electrodes COML formed on a surface of the color filter 82. The drive electrodes COML are formed on a side of the color filter 82 opposite to the glass substrate 81 side thereof. A touch detection electrode TDL, which is a detection electrode of the sensor 50A, is formed on the other surface of the glass substrate 81. A polarizing plate, which is not illustrated, is disposed on the touch detection electrode TDL, and the protection layer PR2 is disposed on the polarizing plate.

For example, in the color filter 82, color filters colored in three colors of red (R), green (G), and blue (B) are periodically aligned, and a set of three colors of R, G, and B is associated with each pixel Pix illustrated in FIG. 13 described above. In the Z direction, the color filter 82 faces the liquid crystal layer 96. The colors of the color filter 82 are not limited to a combination of the three colors of red (R), green (G), and blue (B), and may also be a combination of other colors. For example, the color filter 82 may include white (W). The color filter may not be provided, and in this case, the color will be white. Alternatively, light transmissive resin may be used for the color filter to form white.

The drive electrode COML in the embodiment not only functions as a common drive electrode of the display DP, but also functions as a drive electrode of the sensor 50A. In the present embodiment, one drive electrode COML corresponds to one pixel electrode 92 (pixel electrodes 92 forming one row). In the Z direction, the drive electrode COML of the embodiment faces the pixel electrode 92. A drive signal Vcom is applied to the drive electrode COML from a driver circuit, which is not illustrated, via a contact conductive column having conductivity, which is not illustrated.

The liquid crystal layer 96 modulates the passing light according to the state of electric field and uses, for example, a liquid crystal LC of various modes such as an in-plane switching (IPS) mode including a fringe field switching (FFS) mode, a twisted nematic (TN) mode, a vertical alignment (VA) mode, an electrically controlled birefringence (ECB) mode, or the like.

An orientation film is disposed between the liquid crystal layer 96 and the first substrate 2A, and between the liquid crystal layer 96 and the second substrate 3A. An incident-side polarizing plate may be disposed on the lower surface side of the first substrate 2A.

Figure 20:
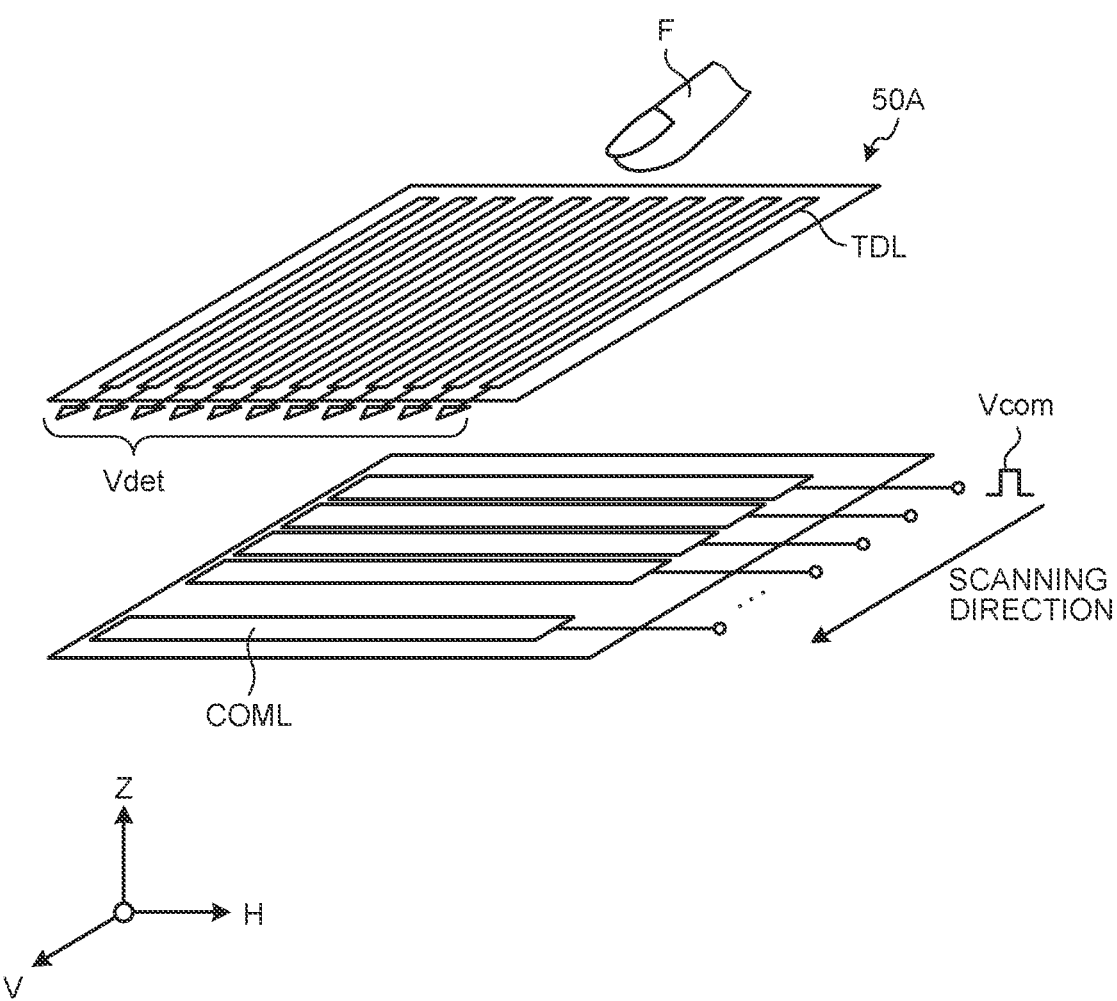
FIG. 20 is a schematic diagram illustrating an example of a main configuration of the sensor.

FIG. 20 is a schematic diagram illustrating an example of a main configuration of the sensor 50A. The drive electrode COML and the touch detection electrode TDL that are provided on the second substrate 3A constitute the sensor 50A of the embodiment. The drive electrode COML may be provided on the first substrate 2A. In this case, for example, the drive electrode COML is insulated from the pixel electrode 92 and the circuit layer 90 and is layered on the rear surface side of the pixel electrode 92.

The drive electrodes COML extend in the H direction and form a plurality of electrode patterns with stripes. When a touch detection operation is performed, the drive signal Vcom is sequentially supplied to each drive electrode COML by the driver circuit described above, and a line-sequential scanning drive is thereby performed in a time divisional manner. A plurality of the touch detection electrodes TDL extend in the V direction and form striped-shape electrode patterns. In the Z direction, the touch detection electrodes TDL face the drive electrodes COML. As is the case with the detection circuit 55, each of the electrode patterns of the touch detection electrodes TDL is coupled to a circuit that performs a touch detection on the basis of the change in capacitance. The electrode patterns in which the drive electrodes COML and the touch detection electrodes TDL intersect with each other generate electrostatic capacitance at the intersecting portions. The electrostatic capacitance is what is called mutual capacitance.

When the sensor 50A performs a touch detection operation, the driver circuit described above line-sequentially scans drive electrode blocks of the drive electrodes COML in a time divisional manner, whereby each detection block is sequentially selected. A touch detection signal Vdet is output from the touch detection electrode TDL, whereby a touch detection of one detection block is performed by the sensor 50A. The electrode patterns in which the drive electrodes COML and the touch detection electrodes TDL are intersecting with each other form capacitive touch sensors in a matrix (row-column configuration). Hence, it is possible to detect a position to or with an external object such as the finger F is in proximity or in contact across the entire display surface of the display area AA. In the third modification, the sensor 50A is provided instead of the sensor 50 in the first embodiment including the detection electrodes 51, 52, 53, and 54 described with reference to FIG. 2.

The pixel electrode 92, the drive electrode COML, and the touch detection electrode TDL are electrodes having light transmissivity formed of a light-transmitting conductive material such as ITO. In the third modification, as illustrated in FIG. 18, the backlight BL emits the light UV and the visible light VL to the liquid crystal display panel PB from the rear surface side.

Figure 21:
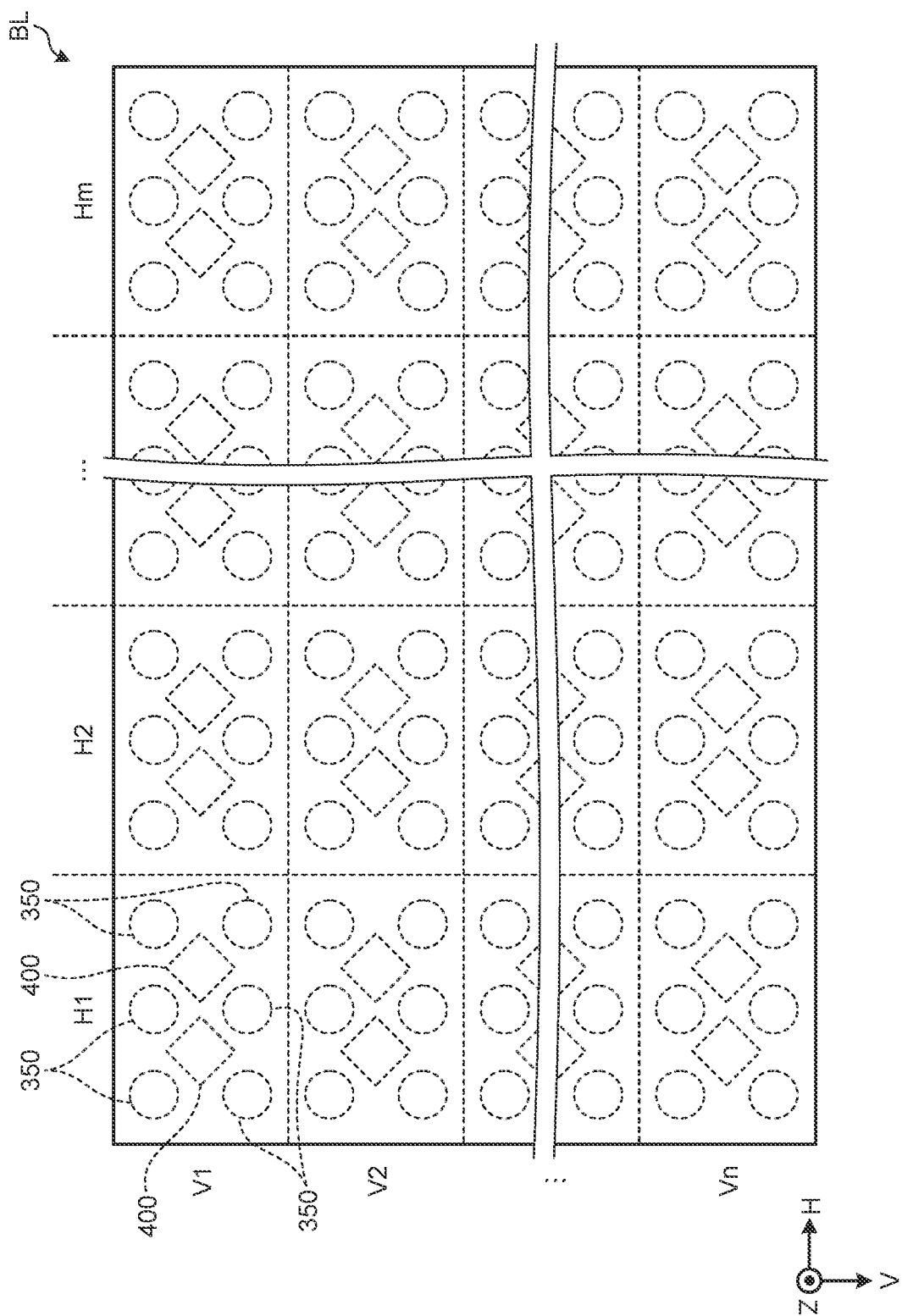
FIG. 21 is a plan view illustrating an example of a configuration of a backlight.

FIG. 21 is a plan view illustrating an example of a configuration of the backlight BL. As illustrated in FIG. 21, the backlight BL in the third modification is divided into m×n divided areas in the H direction and the V direction. In FIG. 21, the division in the H direction is indicated by coordinates H1, H2, . . . , Hm, and the division in the V direction is indicated by coordinates V1, V2, . . . , Vn. Each divided area includes one or more sterilization lamps 400, and one or more visible light sources 350. As is the case with the sterilization lamp in the ultraviolet light emitter 40, the sterilization lamp 400 emits the light UV by being turned ON. As is the case with the visible light source in the visible light emitter 35, the visible light source 350 emits the visible light VL by being turned ON. In one divided area in FIG. 21, six visible light sources 350 are arranged in a three-by-two arrangement in the H direction and the V direction, and two sterilization lamps 400 are arranged in a one-by-two arrangement in the H direction and the V direction. However, this is merely an example, and the arrangements of the sterilization lamps 400 and the visible light sources 350 is not limited thereto and may be changed as appropriate.

In the third modification, the sterilization lamp 400 is turned ON in the divided area overlapping with the position where the external object is detected by the sensor 50A in the H-V plane view. In the third modification, as is the case with the second modification, the emission amount of visible light VL from the visible light sources 350 disposed in the same divided area as that where the sterilization lamps 400 are turned ON, may be reduced than those in the other divided areas.

As described above, according to the third modification, the display DP of the liquid crystal display panel PB is a transmissive liquid crystal display panel and includes the backlight BL that emits visible light from the rear surface side of the display DP. In this manner, the display device 100B including the transmissive liquid crystal display panel can also increase and decrease the emission amount of ultraviolet light.

In the third modification, what is called an in-cell panel is employed in which the sensor 50A and the display DP are integrally provided. However, a specific form of the mutual-capacitance sensor 50A is not limited thereto. What is called an on-cell type in which the sensor 50A and the display DP individually include the drive electrode COML and are provided as individual panels may be employed.

In the above description, the display panel provided with a sterilization device such as the sterilization device 1 is a display panel of a self-light emission type, a reflective liquid crystal display panel, or a transmissive liquid crystal display panel. However, the display panel is not limited thereto. For example, any flat panel display panel such as a semi-transmissive liquid crystal display panel, an electronic paper display device including electrophoretic elements, or the like may also be employed. Needless to say, the size of the display panel is not particularly limited and may be small to large in size.

A configuration including a sterilization device such as the sterilization device 1 is not limited to the display panel. The sterilization device 1 may be employed in any configuration that may require sterilization when an external object such as the finger F is in proximity thereto or in contact therewith.

Other functions and effects brought about by the aspects described in the present embodiment, which are apparent from the description of the present specification, or can be easily assumed by those skilled in the art, are naturally understood to be brought about by the present disclosure.

What is claimed is:

1. A display device comprising:
a display panel including a display surface;
a sensor configured to detect an external object in proximity to or in contact with the display surface;
an ultraviolet light emitter configured to emit ultraviolet light to the display surface; and
a controller configured to control an operation of the ultraviolet light emitter, wherein
the controller gradually increases an emission amount of ultraviolet light from the ultraviolet light emitter with respect to the distance between the object and the display surface as the object approaches the display surface, and gradually reduces the emission amount of ultraviolet light from the ultraviolet light emitter with respect to the distance between the object and the display surface as the object recedes from the display surface.

2. The display device according to claim 1, wherein, a rate of decrease in the emission amount of ultraviolet light with respect to the distance between the object and the display surface as the object recedes from the display surface is smaller than a rate of increase in the emission amount of ultraviolet light with respect to the distance between the object and the display surface as the object approaches the display surface.

3. The display device according to claim 1, wherein
a plurality of the ultraviolet light emitters are provided adjacent to a plurality of partial areas in a plan view,
the partial areas are provided in locations overlapping partial detection areas, respectively,
the controller controls to turn ON one or more of the ultraviolet light emitters to emit the ultraviolet light to one or more of the partial areas each overlapping a partial detection area to or with which the object is in proximity or in contact.

4. The display device according to claim 1, wherein the sensor includes an electrode and is configured to detect the object based on a change in capacitance of the electrode.

5. The display device according to claim 4, wherein a plurality of the electrodes are disposed along an outer periphery of a display area formed in a polygonal shape where an image is displayed on the display surface.

6. The display device according to claim 1, further comprising:
a front light configured to emit visible light to the display panel, wherein
the display panel is a reflective liquid crystal display panel.

7. The display device according to claim 6, wherein
the ultraviolet light is emitted to a part of the display surface to or with which the object is closer or in contact, and
an amount of visible light emitted to the part is smaller than an amount of visible light emitted to another part.

8. The display device according to claim 1, further comprising:
a backlight configured to emit visible light from a rear surface side of the display panel, wherein
the display panel is a transmissive liquid crystal display panel.

9. The display device according to claim 8, wherein
the ultraviolet light is emitted to a part of the display surface to or with which the object is closer or in contact, and
an amount of visible light emitted to the part is smaller than an amount of visible light emitted to another part.

10. A sterilization device comprising:
a sensor configured to detect proximity or contact of an external object;
an ultraviolet light emitter configured to emit ultraviolet light; and
a controller configured to control an operation of the ultraviolet light emitter, wherein
the controller gradually increases an emission amount of ultraviolet light from the ultraviolet light emitter with respect to the distance between the object and the display surface as the object approaches the sensor, and gradually reduces the emission amount of ultraviolet light from the ultraviolet light emitter with respect to the distance between the object and the display surface as the object recedes from the sensor.

11. The sterilization device according to claim 10, wherein a rate of decrease in the emission amount of ultraviolet light with respect to the distance between the object and the sensor as the object recedes from the sensor is smaller than a rate of increase in the emission amount of ultraviolet light with respect to the distance between the object and the sensor as the object approaches the sensor.

12. The sterilization device according to claim 10, wherein
a plurality of the ultraviolet light emitters are provided adjacent to a plurality of partial areas in a plan view,
the partial areas are provided in locations overlapping partial detection areas, respectively,
the controller controls to turn ON one or more of the ultraviolet light emitters to emit the ultraviolet light to one or more of the partial areas each overlapping a partial detection area to or with which the object is in proximity or in contact.

13. The sterilization device according to claim 10, wherein the sensor includes an electrode and is configured to detect the object based on a change in capacitance of the electrode.

14. The sterilization device according to claim 13, wherein a plurality of the electrodes are disposed along an outer periphery of a display area formed in a polygonal shape where an image is displayed by a display panel that displays an image.

15. A display device comprising:
a display panel including a display surface;
a sensor configured to detect an external object in proximity to or in contact with the di splay surface;
an ultraviolet light emitter configured to emit ultraviolet light to the display surface; and
a controller configured to control an operation of the ultraviolet light emitter, wherein
the controller increases an emission amount of ultraviolet light from the ultraviolet light emitter as the object approaches the display surface, and reduces the emission amount of ultraviolet light from the ultraviolet light emitter as the object recedes from the display surface,
wherein a rate of decrease in the emission amount of ultraviolet light with respect to the distance between the object and the display surface as the object recedes from the display surface is smaller than a rate of increase in the emission amount of ultraviolet light with respect to the distance between the object and the display surface as the object approaches the display surface.

16. A sterilization device comprising:
a sensor configured to detect proximity or contact of an external object;
an ultraviolet light emitter configured to emit ultraviolet light; and
a controller configured to control an operation of the ultraviolet light emitter, wherein
the controller increases an emission amount of ultraviolet light from the ultraviolet light emitter as the object approaches the sensor, and reduces the emission amount of ultraviolet light from the ultraviolet light emitter as the object recedes from the sensor,
wherein a rate of decrease in the emission amount of ultraviolet light with respect to the distance between the object and the display surface as the object recedes from the display surface is smaller than a rate of increase in the emission amount of ultraviolet light with respect to the distance between the object and the display surface as the object approaches the display surface.

* * * * *